(12) United States Patent
Kayyali

(10) Patent No.: US 11,419,525 B1
(45) Date of Patent: *Aug. 23, 2022

(54) MEDICAL DEVICE AND METHOD WITH IMPROVED BIOMETRIC VERIFICATION

(71) Applicant: Cleveland Medical Devices Inc., Cleveland, OH (US)

(72) Inventor: Hani Kayyali, Shaker Heights, OH (US)

(73) Assignee: Cleveland Medical Devices Inc., Cleveland, OH (US)

(*) Notice: Subject to any disclaimer, the term of this patent is extended or adjusted under 35 U.S.C. 154(b) by 217 days.

This patent is subject to a terminal disclaimer.

(21) Appl. No.: 16/531,502

(22) Filed: Aug. 5, 2019

Related U.S. Application Data

(63) Continuation of application No. 15/910,068, filed on Mar. 2, 2018, now Pat. No. 10,413,222, which is a continuation of application No. 14/173,897, filed on Feb. 6, 2014, now Pat. No. 9,943,252, which is a
(Continued)

(51) Int. Cl.
A61B 5/00 (2006.01)
A61B 5/1172 (2016.01)
A61B 5/1455 (2006.01)
G16H 40/67 (2018.01)
A61B 5/0205 (2006.01)
A61B 5/318 (2021.01)
A61B 5/369 (2021.01)
A61B 5/389 (2021.01)
A61B 5/398 (2021.01)
G06V 40/10 (2022.01)
A61B 5/087 (2006.01)

(52) U.S. Cl.
CPC .......... A61B 5/1172 (2013.01); A61B 5/0002 (2013.01); A61B 5/0006 (2013.01); A61B 5/0022 (2013.01); A61B 5/0205 (2013.01); A61B 5/1455 (2013.01); A61B 5/14551 (2013.01); A61B 5/318 (2021.01); A61B 5/369 (2021.01); A61B 5/389 (2021.01); A61B 5/398 (2021.01); A61B 5/4806 (2013.01); A61B 5/4809 (2013.01); A61B 5/4815 (2013.01); A61B 5/6826 (2013.01); G06V 40/10 (2022.01); G16H 40/67 (2018.01); A61B 5/087 (2013.01)

(58) Field of Classification Search
None
See application file for complete search history.

(56) References Cited

U.S. PATENT DOCUMENTS 6,425,861 B1 * 7/2002 Haberland ........... A61B 5/0002 600/300
6,643,531 B1 * 11/2003 Katarow ............. A61B 5/1172 600/323

(Continued)

Primary Examiner — Shirley X Jian
(74) Attorney, Agent, or Firm — Brian Kolkowski

(57) ABSTRACT

The present invention is both a device and a method for verifying a subject's identity while using a medical device or undergoing a medical diagnostic or therapeutic procedure, particularly at home or at a remote location. The method and device can be used for inpatient and remote sleep and signal analysis with biometric identification. The present invention is further related to the devices and sensors used in executing the method, and includes various embodiments of a method of inpatient and remote sleep analysis.

20 Claims, 9 Drawing Sheets

Related U.S. Application Data continuation of application No. 12/228,461, filed on Aug. 13, 2008, now Pat. No. 8,679,012.

(56) References Cited

U.S. PATENT DOCUMENTS

| | | | | |
|---|---|---|---|---|
| 6,811,538 B2* | 11/2004 | Westbrook | ............ | A61B 5/0205 600/529 |
| 6,858,006 B2* | 2/2005 | MacCarter | ............ | A61B 5/1135 600/300 |
| 6,945,935 B1* | 9/2005 | Sasse | ............ | G06F 19/00 600/300 |
| 6,993,378 B2* | 1/2006 | Wiederhold | ............ | A61B 5/02055 600/509 |
| 7,279,806 B2* | 10/2007 | Hale | ............ | B60R 25/2009 307/10.4 |
| 7,502,643 B2* | 3/2009 | Farringdon | ............ | A61B 5/721 600/509 |
| 7,609,145 B2* | 10/2009 | Martis | ............ | A61B 5/02438 340/5.1 |
| 7,683,759 B2* | 3/2010 | Martis | ............ | A61B 5/6838 340/5.83 |
| 7,970,450 B2* | 6/2011 | Kroecker | ............ | A61B 5/1112 600/391 |
| 8,033,996 B2* | 10/2011 | Behar | ............ | G06F 3/011 600/300 |
| 8,679,012 B1* | 3/2014 | Kayyali | ............ | A61B 5/318 600/301 |
| 9,202,008 B1* | 12/2015 | Frederick | ............ | A61B 5/7282 |
| 9,492,084 B2* | 11/2016 | Behar | ............ | A61B 5/4866 |
| 9,492,105 B1* | 11/2016 | Kayyali | ............ | A61B 5/0535 |
| 9,750,429 B1* | 9/2017 | Sackner | ............ | A61B 5/6805 |
| 9,943,252 B1* | 4/2018 | Kayyali | ............ | A61B 5/0205 |
| 2002/0188216 A1* | 12/2002 | Kayyali | ............ | A61B 5/6814 600/544 |
| 2005/0113703 A1* | 5/2005 | Farringdon | ............ | A61B 5/0205 600/509 |
| 2006/0035707 A1* | 2/2006 | Nguyen | ............ | G07F 17/323 463/29 |
| 2006/0074280 A1* | 4/2006 | Martis | ............ | A61B 5/14552 600/310 |
| 2006/0075257 A1* | 4/2006 | Martis | ............ | A61B 3/005 713/186 |
| 2010/0234697 A1* | 9/2010 | Walter | ............ | A61B 5/291 600/301 |
| 2016/0048671 A1* | 2/2016 | Munafo | ............ | G06F 21/32 340/5.82 |

* cited by examiner

MEDICAL DEVICE AND METHOD WITH IMPROVED BIOMETRIC VERIFICATION

CROSS-REFERENCE TO RELATED APPLICATIONS

This application is a continuation of U.S. patent application Ser. No. 15/910,068, filed on Mar. 2, 2018, which is a continuation of U.S. patent application Ser. No. 14/173,897, filed on Feb. 6, 2014 and issued as U.S. Pat. No. 9,943,252 on Apr. 17, 2018, which is a continuation of U.S. patent application Ser. No. 12/228,461, filed on Aug. 13, 2008 and issued as U.S. Pat. No. 8,679,012 on Mar. 25, 2014.

BACKGROUND OF THE INVENTION

1. Field of Use

The present invention is both a device and a method for verifying a subject's identity while using a medical device or undergoing a medical diagnostic or therapeutic procedure, particularly at home or at a remote location.

2. Technology Review

Nearly one in seven people in the United States suffer from some type of chronic sleep disorder, and only 50% of people are estimated to get the recommended seven to eight hours of sleep each night. It is further estimated that sleep deprivation and its associated medical and social costs (loss of productivity, industrial accidents, etc.) exceed $150 billion per year. Excessive sleepiness can deteriorate the quality of life and is a major cause of morbidity and mortality due to its role in industrial and transportation accidents. Sleepiness further has undesirable effects on motor vehicle operation, employment, higher earning and job promotion opportunities, education, recreation, and personal life.

Primary sleep disorders affect approximately 50 million Americans of all ages and include narcolepsy, restless legs/periodic leg movement, insomnia, and most commonly, obstructive sleep apnea (OSA). OSA's prevalence in society is comparable with diabetes, asthma, and the lifetime risk of colon cancer. OSA is grossly under diagnosed with an estimated 80-90% of persons afflicted having not received a clinical diagnosis. Secondary sleep disorders include loss of sleep due to pain associated with chronic infections, neurological/psychiatric disorders, or alcohol/substance abuse disorders.

Sleeping disorders are currently diagnosed by two general methods. Subjective methods, such as the Epworth and Standford Sleepiness Scale, generally involve questionnaires that require patients to answer a series of qualitative questions regarding their sleepiness during the day. With these subjective methods, however, it is found that the patients usually underestimate their level of sleepiness or they deliberately falsify their responses because of their concern regarding punitive action or as an effort to obtain restricted stimulant medication.

The second group of methods uses a combination of sensors and various physiological measurements to examine a subject's sleep health. An example of such an approach is the use of all-night polysomnography (PSG) to evaluate a subject's sleep architecture (e.g., obtaining respiratory disturbance index to diagnose sleep apnea). Sleep testing in this manner typically requires patients to spend the night in a sleep laboratory connected to multiple sensors while they attempt to sleep. Because it is conducted in a laboratory setting, sleep testing cannot provide information about a patient's regular sleeping environment, such as noise, light, or allergens. Sleep testing performed in a laboratory setting can also be difficult to conduct because of a patient's travel concerns or anxiety related to sleeping away from home. Many patients also exhibit a "first night effect" related to a change in sleeping environment. The first night effect often requires a second night in the sleep laboratory to obtain accurate results. Therefore, the first night effect can easily double the cost of conducting a sleep test in a sleep laboratory. Further, these same problems and concerns are equally applicable to sleep therapeutic procedures conducted in a sleep laboratory.

To address the difficulties of conducting sleep testing and therapy in a sleep laboratory, various methods and devices have been developed to perform remote sleep testing and/or therapy from a subject's regular sleeping location. Currently, methods and devices exist which allow remote sleep testing and therapy to be performed using either a remotely attended study or a remote unattended study. In a remotely attended sleep test or therapeutic procedure, data from various sensors is transmitted from the study site to a remote site for analysis in real-time or near real-time. Data transmitted not only includes sleep sensor measurements, but can also include audio and video data, allowing a remote attendant to visually and/or audibly monitor a sleep study in addition to monitoring standard physiological parameters. In unattended remote sleep tests or therapeutic procedures, data from various sleep sensors is simply stored during the sleep test and analyzed by a medical professional at a later time.

The use of remote sleep testing and therapy has many advantages, including alleviation of first night effect, and reduction of cost and inconvenience associated with a subject's being required to travel to a sleep laboratory to undergo these procedures. For these reasons and others, remote sleep testing and therapy has grown significantly in recent times and is likely to continue to increase in prevalence as it becomes more reliable and as understanding of the importance of sleep health continues to increase.

One area of concern associated with the increasing use of unattended remote sleep studies is that of ensuring that the subject for whom a sleep study was intended, is the subject from whom sleep data was in fact collected. Various reasons exist for a subject to falsify sleep test data by having another individual undergo sleep testing in his or her place. Among the most compelling reasons are fear of lifestyle change, fear of possible punitive action and fear that one's employment or means of support may be affected by a positive diagnosis for a sleep disorder. The temptation to falsify sleep test results is of special concern among individuals performing sleep-critical jobs such as over-the-road truck drivers, airline pilots and others similarly employed. Not only are there strong reasons for these individuals to falsify sleep test results because of possible effects on job stability, but the danger posed both to themselves and others such as airline passengers and other drivers is significant.

One method of addressing this concern is to incorporate a subject identification process into the sleep testing procedure. Such a step would serve to ensure that sleep test data is in fact collected from the individual for whom the sleep test was intended. Currently, none of the methods or devices used for unattended remote sleep testing and therapy provide means for verification of patient identity during a sleep diagnostic or therapeutic procedure. Further, none of the methods or devices presently used for sleep testing and sleep therapy performed in a sleep laboratory or performed using remote attendance provide means for simple, secure, biometric verification of subject identity.

It is therefore an object of the present invention to provide a method and device for conducting biometric verification of subject identity as part of unattended remote sleep testing and sleep therapy procedures. It is another object of the present invention to provide a method or device for conducting biometric verification of subject identity as part of sleep testing and sleep therapy procedures conducted in a sleep laboratory as well as sleep testing and sleep therapy procedures which are remotely attended. It is still another object of the present invention to provide a method or device by which biometric identification of a sleep test subject or sleep therapy subject can be performed using a portable sleep diagnostic and/or therapeutic system while the subject sleeps. It is another object of the present invention to provide a method or device for securely handling biometric data in compliance with HIPAA and HCFA standards. It is another object of the present invention to provide a method or device for coordinating the step of biometric verification of a subject's identity with various physical or physiological parameters measured from the subject. It is still another object of the present invention to provide a method or device for coordinating biometric verification of subject identity with sleep onset during sleep testing. Still another object of the present invention is to provide correlation between biometric verification of subject identity and heart rate measured using both ECG and pulse oximetry to ensure that a subject for whom a sleep test was intended is the subject from whom test measurements were acquired.

SUMMARY OF THE INVENTION

The present invention is both a device and a method for verifying a subject's identity while using a medical device or undergoing a medical diagnostic or therapeutic procedure, particularly at home or at a remote location. The method and device can be used for inpatient and remote sleep and signal analysis with biometric identification. The present invention is further related to the devices and sensors used in executing the method, and includes various embodiments of a method of inpatient and remote sleep analysis.

The device and method of the present invention is particularly useful in a number of applications. These applications include but are not limited to conducting sleep analysis wherein verification of subject identity during the sleep analysis procedure is necessary. Some of the applications for example include but are not limited to testing of truck drivers, airline pilots, automobile drivers, other sleep critical jobs and the like. The device and method of the present invention is particularly useful when remotely testing a subject with a sleeping disorder, more particularly obstructive sleep apnea. The device and method of the present invention includes any useful applications, which will be apparent to those skilled in the art.

The device and method of the present invention prevents misuse or fraud when using the invention to test a subject, ensuring that the subject being tested is in fact the subject for whom the test was intended. Numerous methods are disclosed to prevent the subject from misleading a clinician or doctor. Among the methods disclosed is the use of biometric parameters to verify a subject's identity. Biometric parameters for example include fingerprints, voice, physiological information, retinal scan, palm recognition, and the like. Also disclosed are methods of preventing misuse or fraud when testing a subject, which include random, periodic or continuous biometric verification of subject identity during a test. Other methods disclosed in the present invention include correlation of physiologic parameters pertaining to a subject's sleep quality or the time of sleep onset with the step of biometric verification. Still other methods exist, many of which will be clear combinations of the steps disclosed herein.

The device and method of the present invention further provides for secure handling of a subject's biometric and medical information. To this end, the device and method of the present invention includes means whereby biometric data can be temporarily stored, easily erased, and not communicated other devices. Further provisions of the present invention to ensure secure handling of a subject's biometric and medical data include the use of HIPAA and HCFA compliant transfer of such data for applications in which transfer of such data is necessary or desired.

Examples of various embodiments of the present invention are as follows. In one embodiment, the present invention includes a sleep diagnostic device comprising at least three sensors for measuring physiological parameters of a subject related to the subject's quality of sleep and at least one biometric sensor for identifying the subject wherein the at least one biometric sensor is used to authenticate the identity of the subject being tested.

In another embodiment, the present invention includes a sleep diagnostic device comprising at least three sensors for measuring physiological parameters of a subject related to the subject's quality of sleep, one of the at least three sensors used to measure airflow from a nasal canula, and at least one biometric sensor for identifying the subject wherein the at least one biometric sensor is used to authenticate the identity of the subject being tested.

In still another embodiment, the present invention includes a sleep diagnostic device comprising at least four sensors for measuring physiological parameters of a subject related to the subject's quality of sleep wherein the at least four sensors for measuring physiological parameters are used to measure ventilation, respiratory effort, ECG or heart rate, and blood oxygen saturation and at least one biometric sensor wherein the at least one biometric sensor is used to authenticate the identity of the subject being tested.

In even another embodiment, the present invention includes a sleep diagnostic device comprising at least seven sensors for measuring physiological parameters of a subject related to the subject's quality of sleep wherein the at least seven sensors for measuring physiological parameters are used to measure ventilation, respiratory effort, ECG or heart rate, blood oxygen saturation, EEG, EOG, and EMG and at least one biometric sensor wherein the at least one biometric sensor is used to authenticate the identity of the subject being tested.

In even still another embodiment, the present invention includes a sleep diagnostic device comprising at least one sensor for measuring physiological parameters of a subject related to the subject's quality of sleep, at least one biometric sensor for identifying the subject, and a processor wherein the at least one biometric sensor is used to collect biometric data, the processor compares the collected biometric data with biometric data previously collected from the subject, and the processor outputs verification of the identity of the subject whose quality of sleep is being measured without outputting the subject's biometric data.

In even still another embodiment, the present invention includes a sleep diagnostic device comprising at least one sensor for measuring physiological parameters of a subject related to the subject's quality of sleep and at least one biometric sensor for identifying the subject wherein the sleep diagnostic device is used to collect biometric data, compare biometric data with previously collected biometric data, and securely exchange information with an external device.

In still yet another embodiment, the present invention includes coordinating the step of biometric verification of subject identity with various physical and physiological parameters as measured by the various sensors used with the present invention.

In still yet another embodiment, the present invention includes a method of performing sleep analysis or diagnosis comprising the steps of measuring at least one physiological parameter related to the quality of a subject's sleep, determining a sleep onset time for the subject based at least in part on the at least one physiological parameter, measuring at least one biometric parameter of the subject about the sleep onset time of the subject, and comparing the measured at least one biometric parameter of the subject to previously obtained biometric data of the subject.

In still yet another embodiment, the present invention includes a method of performing sleep analysis or diagnosis of a sleep disorder comprising the steps of coordinating heart rate as measured with ECG electrodes and heart rate measured using pulse oximetry in combination with biometric identification to further ensure that a subject for whom a sleep test was intended is the subject from whom sleep test data was collected.

In still yet another embodiment, the present invention includes a method of performing sleep analysis or diagnosis comprising the steps of measuring at least one physiological parameter related to the quality of a subject's sleep, determining a sleep onset time for the subject based at least in part on the at least one physiological parameter, measuring at least one biometric parameter of the subject, and comparing the measured at least one biometric parameter of the subject to previously obtained biometric data of the subject wherein the subject's quality of sleep is measured for at least two hours after the sleep onset time of the subject.

Additional features and advantages of the invention will be set forth in the detailed description that follows, and in part will be readily apparent to those skilled in the art from that description or recognized by practicing the invention as described herein, including the detailed description that follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and, together with the description, serve to explain the principles and operation of the invention.

DESCRIPTION OF THE PREFERRED EMBODIMENTS

Figure 1:
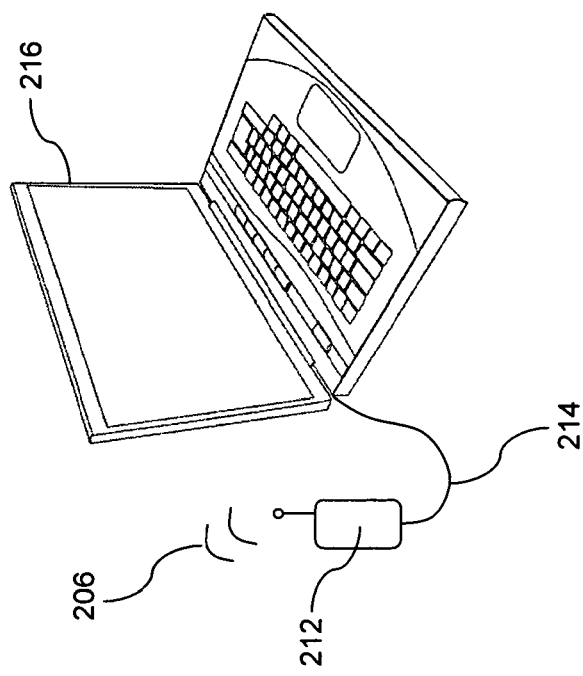
FIG. 1 Schematic diagram of a subject using one embodiment of the medical device and/or method with improved biometric verification.
Figure 1:
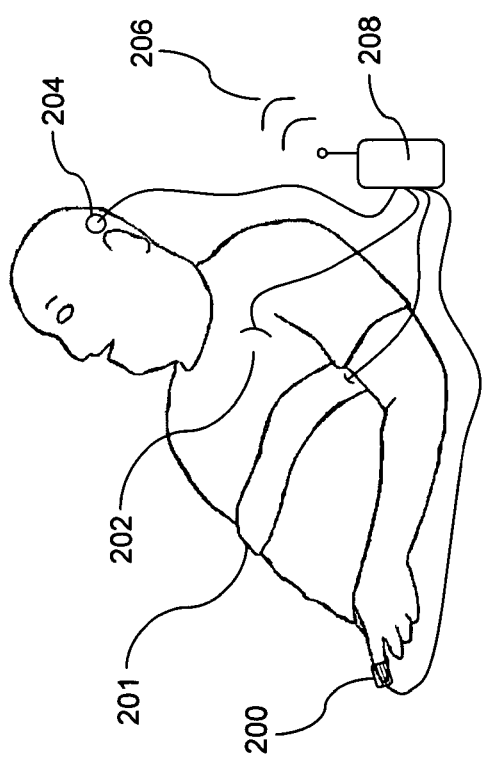

The present invention is related to both a method and device for verifying a subject's identity while using a medical device or undergoing a medical diagnostic or therapeutic procedure. The present invention is further related to the devices and sensors used in executing the method and includes, but is not limited to, various embodiments of a method and device used to verify a subject's identity and perform inpatient and remote sleep testing and analysis. Although the various embodiments described below primarily include a method and device for sleep analysis, it is not intended that the present invention be limited to such applications. Various other embodiments of the present invention using other medical devices will be apparent to those skilled in the art. Examples of such other embodiments include, but are not limited to, the use of other devices such as blood alcohol level sensors, heart rate monitors, sleep therapeutic devices, oxygen saturation devices, pharmaceutical delivery devices and various other medical diagnostic and therapeutic devices.

Various embodiments of the present invention may include a step for determining whether the subject being analyzed for a sleep disorder maintained a normal sleeping pattern prior to the analysis. This step can be performed or accomplished a number of ways. In the simplest form, the subject can be questioned regarding his or her previous sleep patterns. In a somewhat more complex form the subject can be requested to fill out a questionnaire, which then can be graded to determine whether his or her previous sleep patterns where normal (or appeared normal). In an even more complex form the subject might undergo all night polysomnography to evaluate the subject's sleep architecture (e.g., obtaining respiratory disturbance index to diagnose sleep apnea). One of the objectives of this step is to ensure that the results of the subject's brain wave analysis are not the result of or affected by the subject's previous environmental factors i.e., intentional lack of sleep, etc. It is clear that there are numerous ways beyond those examples previously mentioned of determining whether the subject being analyzed maintained or thought they were maintaining a normal sleeping pattern prior to analysis, therefore the examples given above are included as exemplary rather than as a limitation, and those ways of determining whether the subject maintained or thought they were maintaining a normal sleeping pattern known to those skilled in the art are considered to be included in the present invention.

Various embodiments of the present invention may include the step of conducting an inpatient or remote sleep analysis that is attended from a remote location. Such remote attendance can be accomplished by an individual in a remote location (a remote monitor) periodically or continuously viewing the data transmitted from the remote or in-home data acquisition system, including signals from the sensors applied to the subject including biometric signals, signals from the environmental sensors, and a pre-processed signal or signals based at least in part on at least one of the sensors. Preferably, the remote monitor is capable of communicating with the subject, subject's assistant, or other individual near the subject. Such communication allows the remote monitor to provide instructions to the subject, subject's assistant, or other individual near the subject, for example, to adjust a sensor, close window blinds, remove a source of noise, or wake the subject. More preferably, the remote monitor is capable of two-way communication with the subject, subject's assistant, or other individual near the subject. Such communication allows the subject, subject's assistant, or other individual close to the subject to ask the remote monitor questions, for example, to clarify instructions. Depending on the setting for the test this other individual may be a nurse or trained technician at the hospital, nursing home or skilled medical facility. In other settings, it may be any other individual trained in the placement and hookup of the sensors. In still other settings, it might be the subject themselves who could be directed by the monitor as to sensor adjustment, placement and hookup.

Various embodiments of the present invention include an interface box which is preferably used to protect one or more electrical components and allow for the connection of various sensors to the electrical components inside the interface box. The interface box is preferably is secured to or held by the subject. The box also preferably has electrical connectors incorporated in to its structure, so that various sensors can be connected to the box and through to the electrical components inside the interface box. Preferably the connectors incorporated into the interface box are no touch connectors which enable connections to commercially available electrodes and sensors. The interface box preferably has at least one air port connection to one or more internal sensors, such as one or more pressure transducers or other sensors. The interface box more preferably has at least two air port connections to one or more internal sensors, such as one or more pressure transducers or other sensors. The interface box can be constructed from most any rigid material; including, but not limited to, various types of wood, various types of plastics, various types of polymers, various types of resin, various types of ceramics, various types of metals, and various types of composite materials. Preferably the box is constructed of an electrically insulative and light weight material such as a type of plastic, rigid polymer, fiberglass, carbon fiber composite, or other material with similar characteristics.

Various embodiments of the present invention may include the step of applying one or more sensors to the subject. Preferably at least three sensors are applied to the subject, more preferably at least 4, still more preferably at least five sensors, even more preferably at least 7, most preferably at least 9. The sensors can be applied at a variety of locations. Preferably, the sensors are applied in a physician's office or at a place of business. The physician's place of business includes but is not limited to an office building, a freestanding clinic, location within a hospital, mobile vehicle or trailer, leased space, or similar location. Just as preferably, the sensors could be applied in the subject's home or other sleeping location. The subject's sleeping location includes but is not limited to the subject's home, apartment, and the like, as well as a hotel, nursing facility, or other location where an individual could sleep and where this analysis could be done more controllably and/or less expensively than in a sleep lab or hospital setting. Similarly, the sensors can be applied by a variety of individuals, including but not limited to a physician, nurse, sleep technician, or other healthcare professional. Just as preferably, the sensors could be applied by the subject or the subject's spouse, friend, roommate, or other individual capable of attaching the various sensors. More preferably, the sensors could be applied by the subject or the subject's spouse, friend, roommate, or other individual capable of attaching the various sensors with guidance and instruction. Such guidance and instruction can include static information such as pamphlets, audio recordings (on cassettes, compact discs, and the like), video recordings (on videocassettes, digital video discs, and the like), websites, and the like, as well as dynamic information such as direct real-time communication via telephone, cell phone, videoconference, and the like.

The sensors that are used with various embodiments of the present invention are described herein but can also be any of those known to those skilled in the art for the applications of this method. The collected physiological, kinetic, environmental, and biometric data from the sensors can be obtained by any method known in the art. Preferably those sensors include, but are not limited to, wet or dry electrodes, photodetectors, accelerometers, pneumotachometers, strain gauges, thermal sensors, pH sensors, chemical sensors, gas sensors (such as oxygen and carbon dioxide sensors), transducers, piezo sensors, magnetometers, pressure sensors, static charge-sensitive beds, microphones, audio monitors, video monitors, fingerprint sensors, facial recognition sensors, hand geometry sensors iris and retinal sensors, voice recognition sensors and the like. The invention is envisioned to include those sensors subsequently developed by those skilled in the art to detect these types of signals as well. For example, the sensors can be magnetic sensors. Because electro-physiological signals are, in general, electrical currents that produce associated magnetic fields, the present invention further anticipates methods of sensing those magnetic fields to acquire the signal. For example, new magnetic sensors could collect brain wave signals similar to those that can be obtained through a traditional electrode applied to the subject's scalp.

Various embodiments of the present invention include a step for applying sensors to the subject. This step can be performed or accomplished in a number of ways. In the preferred form, four sensors are applied to the subject to measure three channels of physiologic data, and one channel of biometric data. In a somewhat more complex form, multiple sensors are applied to the subject to collect data sufficient for a full polysomnography (PSG) test. The preferred set of sensors for PSG testing includes sensors for two electroencephalogram (EEG) channels, two (electrooculogram) EOG channels, one chin electromyogram (EMG) channel, one nasal airflow channel, one oral airflow channel, one electrocardiogram (ECG) channel, one thoracic respiratory effort channel, one abdominal respiratory effort channel, one pulse oximetry channel, and one shin or leg EMG channel. More preferably, the minimal set of PSG sensors is augmented with at least one additional channel of EOG, one channel of body position (ex., an accelerometer), one channel of video, and optionally one channel of audio. In an even more complex form, many sensors are applied to the subject to collect full PSG data as well as additional physiological, kinetic, and environmental data. For example, additional EEG electrodes may be applied to the subject to rule out seizure disorders, an esophageal pH sensor may be used to detect acid reflux, and a hygrometer or photometer may be used to detect ambient humidity or light, respectively.

Electro-physiological signals such as those obtained via EEG, ECG, EMG, EOG, electroneurogram (ENG), electroretinogram (ERG), and the like can be collected via electrodes placed at one or several relevant locations on the subject's body. For example, when measuring brain wave or EEG signals, electrodes may be placed at one or several locations on the subject's scalp. In order to obtain a good electro-physiological signal, it is desirable to have low impedances for the electrodes. Typical electrodes placed on the skin may have an impedance in the range of from 5 to 10 k$\Omega$. It is in generally desirable to reduce such impedance levels to below 2 k$\Omega$. A conductive paste or gel may be applied to the electrode to create a connection with an impedance below 2 k$\Omega$. Alternatively or in conjunction with the conductive gel, a subject's skin may be mechanically abraded, the electrode may be amplified, or a dry electrode may be used. Dry physiological recording electrodes of the type described in U.S. Pat. No. 7,032,301 are herein incorporated by reference. Dry electrodes are advantageous because they use no gel that can dry out, skin abrasion or cleaning is unnecessary, and the electrode can be applied in hairy areas such as the scalp. Additionally if electrodes are used as the sensors, preferably at least two electrodes are used for each channel of data—one signal electrode and one reference electrode. Optionally, a single reference electrode may be used for more than one channel.

If electrodes are used to collect cardiac electrical signals such as in an ECG, they may be placed at specific points on the subject's body. The ECG is used to measure the rate and regularity of heartbeats, determine the size and position of the heart chambers assess any damage to the heart, and diagnose sleeping disorders. An ECG is important as a tool to detect the cardiac abnormalities that can be associated with sleep and respiratory-related disorders. Although a full ECG typically involves twelve electrodes, only two are required for many tests such as a sleep study. For example, when two electrodes are used to collect an ECG, preferably one is placed on the subject's left-hand ribcage under the armpit, and the other preferably on the right-hand shoulder near the clavicle bone. Optionally, a full set of twelve ECG electrodes may be used, such as if the subject is suspected to have a cardiac disorder. The specific location of each electrode on a subject's body is well known to those skilled in the art and varies between both individuals and types of subjects. If electrodes are used to collect ECG data, preferably the electrode leads are connected to a device contained in the signal processing module of the data acquisition system used in the present invention that measures potential differences between selected electrodes to produce ECG tracings.

Other sensors can be used to measure various parameters of a subject's respiration. Measurement of respiratory airflow is preferably performed using sensors or devices such as a pneumotachometer, strain gauges, thermal sensors, transducers, piezo sensors, magnetometers, pressure sensors, static charge-sensitive beds, pulse oximeters and the like. These sensors or devices also preferably measure nasal pressure, respiratory inductance plethysmography, thoracic impedance, expired carbon dioxide, tracheal sound, snore sound, blood pressure and the like. Measurement of respiratory effort is preferably measured by a respiration belt, esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

One example of such a sensor for measuring respirations either directly or indirectly is a respiration belt. Respiration belts can be used to measure a subject's abdominal and/or thoracic expansion over a measurement time period. The respiration belts may contain a strain gauge, a pressure transducer, or other sensors that can indirectly measure a subject's respirations and the variability of respirations by providing a signal that correlates to the thoracic/abdominal expansion/contraction of the subject's thoracic/abdominal cavity. If respiration belts are used, they may be placed at one of several locations on the subject's torso or in any other manner known to those skilled in the art. Preferably, when respiration belts are used, they are positioned below the axilla and/or at the level of the umbilicus to measure rib cage and abdominal excursions. More preferably, at least two belts are used, with one positioned at the axilla and the other at the umbilicus.

Another example of a sensor or method for measuring respirations either directly or indirectly is a nasal cannula or a facemask used to measure the subject's respiratory airflow. Nasal or oral airflow can be measured quantitatively and directly with a pneumotachograph consisting of a pressure transducer connected to either a standard oxygen nasal cannula placed in the nose or a facemask over the subject's mouth and nose. Airflow can be estimated by measuring nasal or oral airway pressure that decreases during inspiration and increases during expiration. Inspiration and expiration produce fluctuations on the pressure transducer's signal that is proportional to airflow. A single pressure transducer can be used to measure the combined oral and nasal airflow. Alternatively, the oral and nasal components of these measurements can be acquired directly through the use of at least two pressure transducers, one transducer for each component. Preferably, the pressure transducer(s) are internal to the interface box. If two transducers are used for nasal and oral measurements, preferably each has a separate air port into the interface box. In addition, software filtering can obtain "snore signals" from a single pressure transducer signal by extracting the high frequency portion of the transducer signal. This method eliminates the need for a separate sensor, such as a microphone or an additional pressure transducer, and also reduces the system resources required to detect both snore and airflow. A modified nasal cannula or facemask connected to a carbon dioxide or oxygen sensor may also be used to measure respective concentrations of these gases. In addition, a variety of other sensors can be connected with either a nasal cannula or facemask to measure a subject's respirations either directly or indirectly.

Still another example of a sensor or method of directly or indirectly measuring respiration of the subject is a pulse oximeter. The pulse oximeter can measure the oxygenation of the subject's blood by producing a source of light at two wavelengths (650 nm and 905, 910, or 940 nm). Hemoglobin partially absorbs the light by amounts that differ depending on whether it is saturated or desaturated with oxygen. Calculating the absorption at the two wavelengths leads to an estimate of the proportion of oxygenated hemoglobin. Preferably, pulse oximeters are placed on a subject's earlobe or fingertip. More preferably, the pulse oximeter is placed on the subject's index finger. In one embodiment of the present invention, a pulse oximeter is built-in or hard-wired to the interface box. Alternatively, the pulse oximeter can be a separate unit in communication with the interface box via either a wired or wireless connection.

Other sensors can be used to measure various parameters associated with the subject's movement and posture. For example, kinetic data can be obtained by accelerometers placed on the subject. Alternatively, several accelerometers can be placed in various locations on the subject, for example on the wrists, torso, and legs. These accelerometers can provide both motion and general position/orientation data by measuring gravity. A video signal can also provide some kinetic data after processing. Alternatively, stereo video signals can provide three-dimensional position and motion information. Kinetic data includes but is not limited to frequent tossing and turning indicative of an unsuitable mattress, excessive movement of bedding indicating unsuitable sleeping temperatures, and unusual movement patterns indicating pain. In addition, gyroscopic sensors and the like may also be used.

Environmental data can be collected by video cameras, microphones (to detect noise level, etc.), photodetectors, light meters, thermal sensors, particle detectors, chemical sensors, mold sensors, olfactory sensors, barometers, hygrometers, and the like. Environmental data can provide insight into the subject's sleeping location and habits that is unavailable in the traditional laboratory setting. Environmental data can indicate that the subject's sleeping location is a potential source of the subject's sleeping difficulty. By way of example, but not limitation, environmental data can indicate that the subject's sleeping location has an unsuitable temperature, humidity, light level, noise level, or air quality. For example, these environmental conditions can cause sweating, shivering, sneezing, coughing, noise, and/or motion that disrupts the patient's sleep. The environmental sensors can be placed anywhere in the subject's sleeping location or on the subject, if appropriate. Preferably, the environmental sensors are placed near, but not necessarily on, the subject.

Other sensors or devices can be used to measure and collect data pertaining to a subject's unique physical traits or biometric characteristics. This data can then be used for positive identification of a subject during a medical or therapeutic procedure, and in particular during sleep diagnosis and/or therapy. This data is preferably collected using sensors or devices capable of recording biometric parameters such as hand geometry, vein morphology, fingerprints, DNA characteristics, facial and voice characteristics, iris and retinal characteristics and the like.

One example of such a sensor for measuring a biometric parameter is the fingerprint sensor. The use of fingerprints is a desirable approach to biometric identification in medical and therapeutic applications, and in particular during sleep diagnosis and/or therapy applications because fingerprints are permanent, highly unique, universal and easily collectable. Fingerprints are unique, in part, due to the random variations in fingerprint ridges which lead to formation of other unique features known as minutiae. Examples of minutiae include, but are not limited to, ridge bifurcation, ridge trifurcation, ridge endings, and ridge spurs. Establishment of fingerprint identity is accomplished by recording the location and orientation of a number of these minutiae. Once this information has been recorded and stored, an individual can be subsequently identified by the system by comparison of the newly collected fingerprint data with previously recorded fingerprint data.

Fingerprint sensors employ various methods to collect information used to identify a subject including capacitive, optical, thermal and ultrasonic methods. After data collection, advanced algorithms can be used to isolate and extract the unique features of the fingerprint in order to positively identify a previously identified subject by comparison with existing fingerprint data. One embodiment of the present invention includes the use of at least one fingerprint sensor to provide patient identification during the course of a remote sleep test. Preferably this fingerprint sensor is of the capacitive type. The fingerprint sensor could be integrated into the finger-gripping portion of the pulse oximeter, allowing fingerprint sensing to occur on the same finger as pulse oximetry. Optionally, the fingerprint sensor could be connected to the pulse oximeter in such a way as to allow fingerprint analysis of the finger immediately adjacent to the pulse oximeter. Further optionally, the fingerprint sensor could be attached to the pulse oximeter in such a way that it is independent of the pulse oximeter yet requires use of the fingerprint sensor on the same hand as the pulse oximeter. Still further optionally, fingerprint identification could be performed on multiple fingers using multiple fingerprint sensors used independently of, or in combination with, other sensors.

To ensure patient compliance/authentication for the duration of sleep analysis testing, it is preferable that one or more biometric parameters be verified during the course of a sleep test. For example, a simple, non-invasive fingerprint scan using one of the embodiments described above could be performed continuously, randomly or at periodic intervals during the course of the sleep test to ensure that the individual being tested is the individual for whom the test was intended. Additionally, the step of biometric verification of subject identity could be coordinated with measurements from various other physiologic sensors used in the present invention in order to further ensure that collected test data are recorded from the intended test subject. An example of this approach is the use of blood oxygen saturation as measured by a pulse oximeter to detect sleep onset and, shortly after detection of sleep onset, conducting biometric verification of subject identity. Another example of this approach could include correlation of heart rate as measured by ECG electrodes placed on the subject with heart rate as measured using a pulse oximeter in combination with biometric verification of subject identity. In this example, correlation of heart rate as measured by two different sensors in combination with biometric verification prevents a subject from falsifying certain aspects of the sleep test by placing ECG sensors on a different individual while wearing the pulse oximeter and biometric sensing device. In still other examples, various forms of plethysmography could be correlated with the step of biometric identification to ensure subject compliance with the sleep test. Still many other methods and combinations of coordinating and/or correlating the step of biometric identification with physical and physiological parameters exist and will be apparent to those skilled in the art and the examples above are not intended to limit the present invention.

Because of the sensitive nature of biometric data, it is preferable to collect, maintain and handle this data in a secure and reliable fashion, and in a method that is compatible with HIPAA and HCFA guidelines. In one embodiment of the present invention, the biometric data used to verify subject identity during the course of a sleep test is obtained directly from the subject in the presence of one who can verify the subject's identity using standard methods prior to collection of biometric data. In still another embodiment of the present invention, biometric data can be loaded into the biometric sensor or device from a preexisting data source such as an employee or patient file, or the like. Still other methods exist for acquiring biometric data (e.g. via remote upload), and the present invention is not limited to those methods described above.

Once collected, biometric data can be handled and processed in a variety of ways. In one embodiment of the present invention, biometric data is collected from a biometric sensor or sensors and exported to a data acquisition system where it is processed for use in subject authentication during sleep testing. Optionally, this data could be further sent to a remote location for additional processing or storage for use in future applications. In another embodiment, biometric data is collected from a biometric sensor or sensors and data processing and patient authentication occur within the body of the biometric sensor or the data acquisition device. In this embodiment, sensitive biometric data is not exported to a new location, rather a simple pass/fail result for the authentication test is the only data exported. An advantage of this approach is greater biometric data security, as biometric data would not leave the biometric sensor and could be easily overwritten. Further, such an approach may also alleviate subjects' fears associated with collection of such uniquely identifiable data.

Various embodiments of the present invention include the step of connecting the applied sensors to a data acquisition system. The sensors can be connected to the data acquisition system either before or after they are applied to the subject. As an example of connecting the sensors to the data acquisition system after the sensors are applied to the subject, a physician can apply the sensors to the subject and then send the subject home. While at home, the subject can connect the applied sensors to the data acquisition system. Alternatively, the sensors can be connected to the data acquisition system and then applied to the subject.

The sensors can alternatively be permanently hardwired to at least part of the data acquisition system. More preferably, the sensors are connected to at least part of the data acquisition system via releasable connector. The physiological sensors are generally hardwired (permanently or via releasable connector) to the data acquisition system, but the ongoing evolution in wireless sensor technology may allow sensors to contain wireless transmitters. Optionally, such sensors are wirelessly connected to the data acquisition system. As such, these sensors and the wireless connection method are considered to be part of the present invention. With the advances in microelectromechanical systems (MEMS) sensor technology, the sensors may have integrated analog amplification, integrated A/D converters, and integrated memory cells for calibration, allowing for some signal conditioning directly on the sensor before transmission.

Preferably, the sensors are all connected in the same way at the same time, although this is certainly not required. It is possible, but less preferable, to connect the sensors with a combination of methods (i.e., hardwired or wireless) at a combination of times (i.e., some before application to the subject, and some after application to the subject).

Various embodiments of the present invention use a data acquisition system. The data acquisition system is preferably portable. By portable, it is meant, among other things, that the device is capable of being transported relatively easily. Relative ease in transport means that the device is easily worn and carried, generally in a carrying case, to the point of use or application and then worn by the subject without significantly affecting any range of motion. Furthermore, any components of the data acquisition system that are attached to or worn by the subject, such as the sensors and patient interface box, should also be lightweight. Preferably, these patient-contacting components of the device (including the sensors and the patient interface box) weigh less than about 10 lbs., more preferably less than about 7.5 lbs., even more preferably less than about 5 lbs., and most preferably less than about 2.5 lbs. Thus, the patient-contacting components of the device preferably are battery-powered and use a data storage memory card and/or wireless transmission of data, allowing the subject to be untethered. Furthermore, the entire data acquisition system (including the patient-contacting components as well as any environmental sensors, base station, or other components) preferably should be relatively lightweight. By relatively lightweight, it is meant preferably the entire data acquisition system, including all components such as any processors, computers, video screens, cameras, and the like preferably weigh less in total than about 20 lbs., more preferably less than about 15 lbs., and most preferably less than about 10 lbs. This data acquisition system preferably can fit in a reasonably sized carrying case so the patient or assistant can easily transport the system. By being lightweight and compact, the device should gain greater acceptance for use by the subject.

While the equipment and methods used in the various embodiments of the present invention can be used in rooms or buildings adjacent to the subject's sleeping location, due to the equipment's robust nature these methods are preferably performed over greater distances. Preferably, the subject's sleeping location and the remote locations, for example the location of the remote monitor, are separate buildings. Preferably, the subject's sleeping location is at least 1 mile from the remote location(s) receiving the data; more preferably, the subject's sleeping location is at least 5 miles from the remote location(s) receiving the data; even more preferably, the subject's sleeping location is at least twenty miles from the remote location(s) receiving the data; still more preferably, the subject's sleeping location is at least fifty miles from the remote location(s) receiving the data; still even more preferably, the subject's sleeping location is at least two hundred-fifty miles from the remote location(s) receiving the data; more preferably, the subject's sleeping location is in a different state from the remote location(s) receiving the data; and most preferably, the subject's sleeping location is in a different country from the remote location(s) receiving the data.

Various embodiments of the present invention use a data acquisition system capable of receiving signals from the sensors applied to the subject and capable of retransmitting the signals or transmitting another signal based at least in part on at least one of the signals. In its simplest form, the data acquisition system preferably should interface with the sensors applied to the subject and retransmit the signals from the sensors. Preferably, the data acquisition system wirelessly transmits the signals from the sensors. Optionally, the data acquisition system also pre-processes the signals from the sensors and transmits the pre-processed signals. Further optionally, the data acquisition is also capable of storing the signals from the sensors and/or any pre-processed signals.

Various embodiments of the present invention use a data acquisition system capable of storing and/or retransmitting the signals from the sensors or storing and/or transmitting another signal based at least in part on at least one of the signals. The data acquisition system can be programmed to send all signal data to the removable memory, to transmit all data, or to both transmit all data and send a copy of the data to the removable memory. When the data acquisition system is programmed to store a signal or pre-processed signal, the signals from the sensors can be saved on a medium in order to be retrieved and analyzed at a later date. Media on which data can be saved include, but are not limited to chart recorders, hard drive, floppy disks, computer networks, optical storage, solid-state memory, magnetic tape, punch cards, etc. Preferably, data are stored on removable memory. For both storing and transmitting or retransmitting data, flexible use of removable memory can either buffer signal data or store the data for later transmission. Preferably, nonvolatile removable memory can be used to customize the system's buffering capacity and completely store the data.

If the data acquisition system is configured to transmit the data, the removable memory acts as a buffer. In this situation, if the data acquisition system loses its connection with the receiving station, the data acquisition system will temporarily store the data in the removable memory until the connection is restored and data transmission can resume. If however the data acquisition system is configured to send all data to the removable memory for storage, then the system does not transmit any information at that time. In this situation, the data stored on the removable memory can be retrieved by either transmission from the data acquisition system, or by removing the memory for direct reading.

The method of directly reading will depend on the format of the removable memory. Preferably the removable memory is easily removable and can be removed instantly or almost instantly without tools. The memory is preferably in the form of a card and most preferably in the form of a small easily removable card with an imprint (or upper or lower surface) area of less than about two sq. in. If the removable memory is being used for data storage, preferably it can write data as fast as it is produced by the system, and it possesses enough memory capacity for the duration of the test. These demands will obviously depend on the type of test being conducted, tests requiring more sensors, higher sampling rates, and longer duration of testing will require faster write speeds and larger data capacity. The type of removable memory used can be almost any type that meets the needs of the test being applied. Some examples of the possible types of memory that could be used include but are not limited to Flash Memory such as CompactFlash, SmartMedia, Miniature Card, SD/MMC, Memory Stick, or xD-Picture Card. Alternatively, a portable hard drive, CD-RW burner, DVD-RW burner or other data storage peripheral could be used. Preferably, a SD/MMC—flash memory card is used due to its small size. A PCMCIA card is least preferable because of the size and weight.

When the data acquisition system is programmed to retransmit the signals from the sensors, preferably the data acquisition system transmits the signals to a processor for analysis. More preferably, the data acquisition system immediately retransmits the signals to a processor for analysis. Optionally, the data acquisition system receives the signals from one or more of the aforementioned sensors and stores the signals for later transmission and analysis. Optionally, the data acquisition system both stores the signals and immediately retransmits the signals.

When the data acquisition system is programmed to retransmit the signals from the sensors or transmit a signal based at least in part on the signal from the sensors (collectively "to transmit" in this section), the data acquisition system can transmit through either a wireless system, a tethered system, or some combination thereof. When the system is configured to transmit data, preferably the data transmission step utilizes a two-way (bi-directional) data transmission. Using two-way data transmission significantly increases data integrity. By transmitting redundant information, the receiver (the processor, monitoring station, or the like) can recognize errors and request a renewed transmission of the data. In the presence of excessive transmission problems, such as transmission over excessive distances or obstacles absorbing the signals, the data acquisition system can control the data transmission or independently manipulate the data. With control of data transmission it is also possible to control or re-set the parameters of the system, e.g., changing the transmission channel or encryption scheme. For example, if the signal transmitted is superimposed by other sources of interference, the receiving component could secure a flawless transmission by changing the channel. Another example would be if the transmitted signal is too weak, the receiving component could transmit a command to increase the transmitting power. Still another example would be for the receiving component to change the data format of the transmission, e.g., in order to increase the redundant information in the data flow. Increased redundancy allows easier detection and correction of transmission errors. In this way, safe data transmissions are possible even with the poorest transmission qualities. This technique opens a simple way to reduce the transmission power requirements, thereby reducing the energy requirements and providing longer battery life. Another advantage of a bi-directional digital data transmission lies in the possibility of transmitting test codes in order to filter out external interferences, for example, refraction or scatter from the transmission current. In this way, it is possible to reconstruct falsely transmitted data.

All of the preferable embodiments of this method employ a wireless data acquisition system. This wireless data acquisition system consists of several components, each wirelessly connected. Data is collected from the sensors described above by a patient interface box. The patient interface box then wirelessly transmits the data to a separate signal pre-processing module, which then wirelessly transmits the pre-processed signal to a receiver. Alternatively, the patient interface box processes the signal and then directly transmits the processed signal directly to the receiver using wireless technology. Further alternatively, the patient interface box wirelessly transmits the signals to the receiver, which then pre-processes the signal. Preferably, the wireless technology used by the data acquisition system components is radio frequency based. Most preferably, the wireless technology is digital radio frequency based. The signals from the sensors and/or the pre-processed signals are transmitted wirelessly to a receiver, which can be a base station, a transceiver hooked to a computer, a personal digital assistant (PDA), a cellular phone, a wireless network, or the like. Most preferably, the physiological signals are transmitted wirelessly in digital format to a receiver.

Wireless signals between the wireless data acquisition system components are both received and transmitted via frequencies preferably less than about 2.0 GHz. More preferably, the frequencies are primarily 902-928 MHz, but Wireless Medical Telemetry Bands (WMTS), 608-614 MHz, 1395-1400 MHz, or 1429-1432 MHz can also be used. The present invention may also use other less preferable frequencies above 2.0 GHz for data transmission, including but not limited to such standards as Bluetooth, WiFi, IEEE 802.11, and the like.

When a component of the wireless data acquisition system is configured to wirelessly transmit data, it is preferably capable of conducting a radio frequency (RF) sweep to detect an occupied frequency or possible interference. The system is capable of operating in either "manual" or "automatic" mode. In the manual mode, the system conducts an RF sweep and displays the results of the scan to the system monitor. The user of the system can then manually choose which frequency or channel to use for data transmission. In automatic mode, the system conducts a RF sweep and automatically chooses which frequencies to use for data transmission. The system also preferably employs a form of frequency hopping to avoid interference and improve security. The system scans the RF environment then picks a channel over which to transmit based on the amount of interference occurring in the frequency range.

The receiver (base station, remote communication station, or the like) of various embodiments of the wireless data acquisition system can be any device known to receive RF transmissions used by those skilled in the art to receive transmissions of data. By way of example but not limitation, the receiver can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the receiver can further transmit data to another device and/or back. Further optionally, two different receivers can be used, one for receiving transmitted data and another for sending data. For example, with the wireless data acquisition system used in the present invention, the receiver can be a wireless router that establishes a broadband Internet connection and transmits the physiological signal to a remote Internet site for analysis, preferably by the subject's physician or another clinician. Other examples of a receiver are a PDA, computer, or cell phone that receives the data transmission, optionally re-processes the information, and re-transmits the information via cell towers, land phone lines, or cable to a remote processor or remote monitoring site for analysis. Other examples of a receiver are a computer or processor that receives the data transmission and displays the data or records it on some recording medium that can be displayed or transferred for analysis at a later time.

The preferred embodiment of secure data transmission that is compatible with HIPAA and HCFA guidelines will be implemented using a virtual private network. More preferably, the virtual private network will be implemented using a specialized security appliance, such as the PIX 506E, from Cisco Systems, Inc, capable of implementing IKE and IPSec VPN standards using data encryption techniques such as 168-bit 3DES, 256-bit AES, and the like. Still more preferably, secure transmission will be provided by a $3^{rd}$ party service provider or by the healthcare facility's information technology department. The system will offer configuration management facilities to allow it to adapt to changing guidelines for protecting patient health information (PHI).

Preferably, the data acquisition system retransmits the signals from the sensors applied to the subject or transmits a signal based at least in part on at least one of the physiological, kinetic, or environmental signals at substantially a same time as the signal is received or generated. At substantially the same time preferably means within approximately one hour. More preferably, at substantially the same time means within thirty minutes. Still more preferably, at substantially the same time means within ten minutes. Still more preferably, at substantially the same time means within approximately one minute. Still more preferably, at substantially the same time means within milliseconds of when the signal is received or generated. Most preferably, a substantially same time means that the signal is transmitted or retransmitted at a nearly instantaneous time as it is received or generated. Transmitting or retransmitting the signal at substantially a same time allows the physician or monitoring service to review the subject's physiological and kinetic signals and the environmental signals and if necessary to make a determination, which could include modifying the patient's treatment protocols or asking the subject to adjust the sensors.

Various embodiments of the present invention include a step of monitoring a patient from a separate monitoring location. Data transmitted in a remote monitoring application may include, but are not limited to, physiological data, kinetic data, environmental data, audio, and/or video recording. It is preferable that both audio and video communications be components of the envisioned system in order to provide interaction between patient and caregiver when desired.

The envisioned remote monitoring step will require data processing, storage, and transmission. This step may be completed or accomplished in one or more modules of the data acquisition system. The preferred embodiment realizes the remote system as two separate components with a patient interface module that can collect, digitize, store, and transmit data to a base station module that can store, process, compress, encrypt, and transmit data to a remote monitoring location.

Signal quality of the signals from all the sensors can be affected by the posture and movement of the subject. Therefore, the invention preferably incorporates a step to more completely remove motion and other artifacts by firmware and/or software correction that utilizes information collected preferably from a sensor or device to detect body motion, and more preferably from an accelerometer.

Turning now to a description of the figures, FIG. 1 shows a schematic diagram of a subject using one embodiment of the present invention. In FIG. 1, a data acquisition device 208 receives signals from various sensors placed on the subject 200, 201, 202, 204. These sensors can be biometric sensors 200, respiratory sensors 201, ECG sensors 202, EEG sensors 204 or any of the other sensors described herein or known in the art. Although only four types of sensors are shown, the data acquisition device is capable of accepting input signals from multiple additional sensors or using as few as two sensors. The data acquisition device can store the data received from the sensors, transmit the data to a remote location, or both. In this case, data is transmitted via wireless signal 206 to a base station 212 which receives the signal 206 and transfers the data to an external programming and analysis device 216, shown here as a notebook computer, via a data interface cable 214. The external programming and analysis device 216 can then further transmit sleep data to a remote location using the internet or other communication means (not shown).

Figure 2:
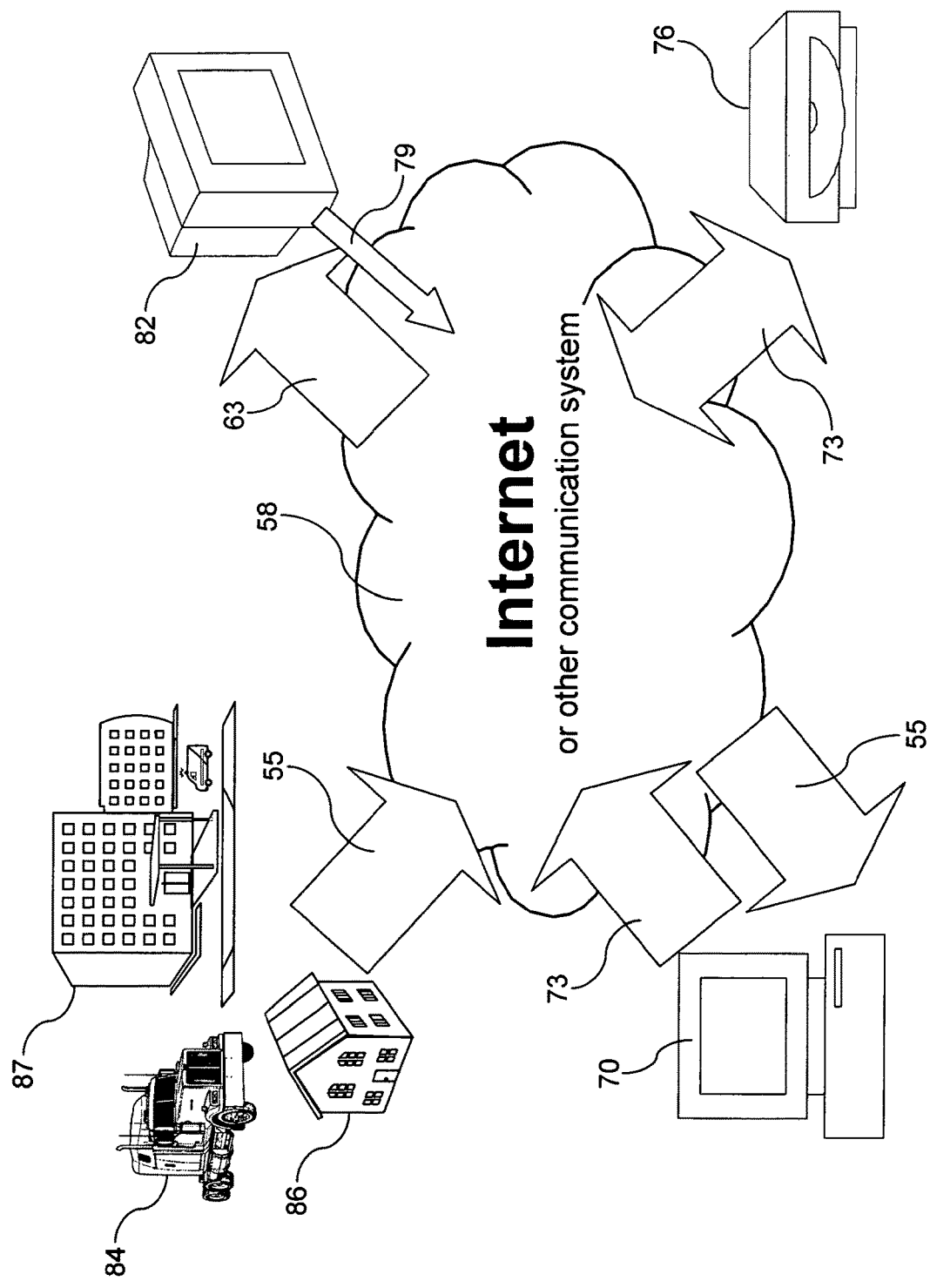
FIG. 2 Schematic diagram of the data transfer and sharing devices and/or processes of one embodiment of the medical device and method with improved biometric verification.

FIG. 2 is a schematic of one embodiment of the data acquisition device and system of the present invention. In FIG. 2, a data acquisition system (similar to that shown in FIG. 3) is used to receive, filter, and optionally analyze signals from sensors (not shown) on a subject (not shown). The data acquisition system (shown in FIG. 3) transmits a signal based, at least in part, on one or more of the signals from the sensors on the subject. The data acquisition device and system transmits the signal 55 from the subject's home 86, a hospital 87, or even a mobile remote location such as a sleeper of a semi-trailer truck 84 to a server 70 for analysis. The signal is transmitted over the internet or other communication system 58. The signal 55 that is transmitted over the internet or other communication system 58 can be compressed to provide better resolution or greater efficiency. The server 70 in this embodiment may also perform data analysis (not shown). The analyzed data 73 is then entered into a database 76. The analyzed data 73 in the database 76 can then be requested 79 and sent 63 to review stations 82 anywhere in the world via the internet or other communication system 58 for further analysis and review by clinicians, technicians, researchers, physicians and the like. The communications systems used for data transmission need not be the same at all stages. For example, a cellular network can be used to transmit data between the subject's home 86 and the remote analysis server 70. The internet can then be used to transmit data between the remote analysis server 70 and the database 76. Finally in this example, a LAN could be used to transmit data between the database 76 and a review station 82.

Figure 3:
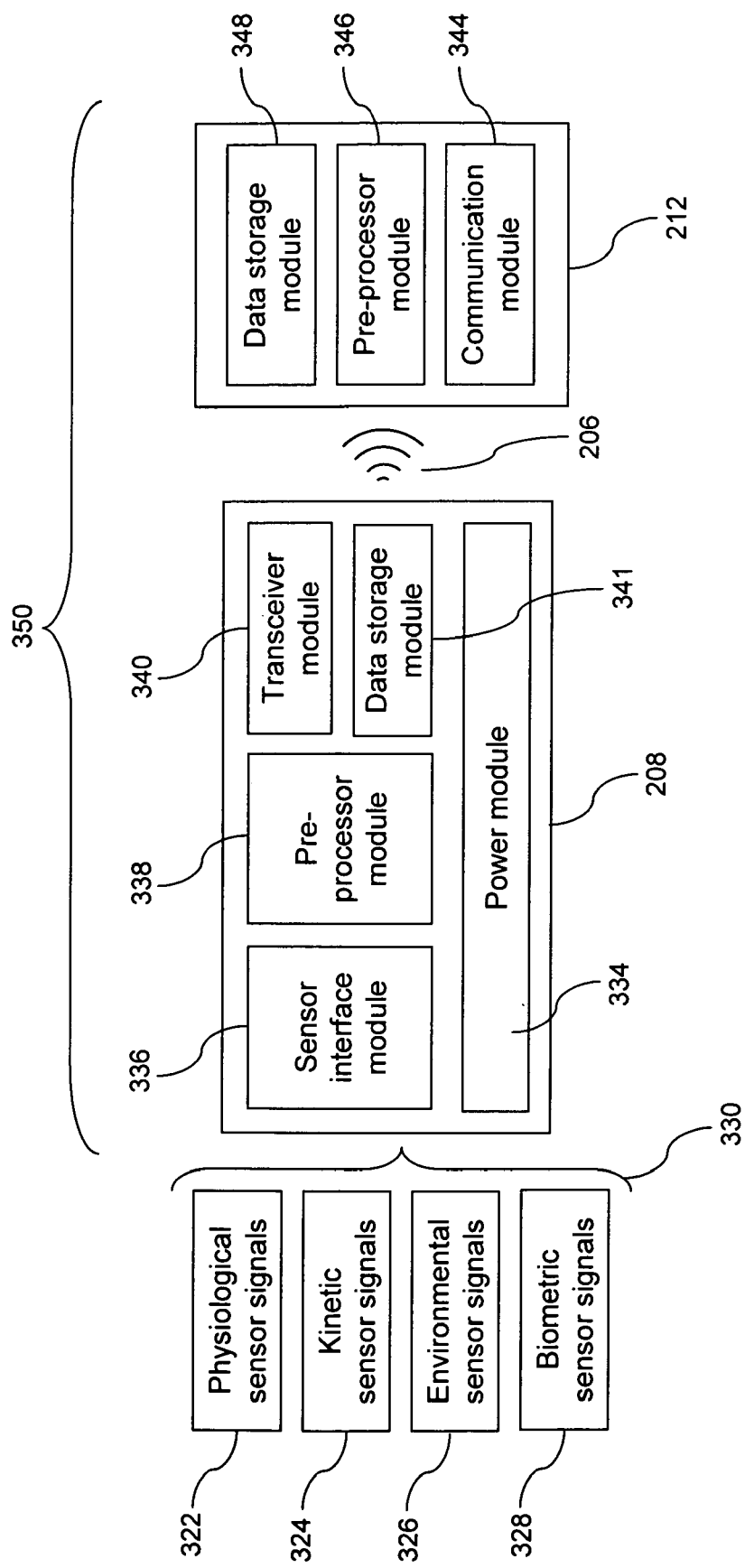
FIG. 3 Block diagram of the data acquisition system of one embodiment of the present invention.

FIG. 3 is a block diagram showing the data flow through the data acquisition system 350 used in certain embodiments of the present invention. In this embodiment, various sensors generate physiological signals 322, kinetic signals 324, environmental signals 326, and biometric signals 328. The sensor signals 330 are input into the data acquisition system 350, consisting of (a) a data acquisition device 208 containing a sensor interface module 336, a preprocessor module 338, a transceiver module 340, a data storage module 341, and a power module 334, and (b) a base station 212 containing a storage module 348, a second pre-processor module 346, and a communication module 344. Typically, the data acquisition device 208 is worn by the subject during the test period. For portability of the data acquisition device 208, the power module 334 can be battery-powered. The data acquisition device 208 sends data via wireless signal 206 to the base station 212. The base station 212 uses the communication module 344 to retransmit the signals from the sensors 330 and/or transmit signals based at least in part on at least one of the signals to remote stations (not shown). Optionally, all sensor signals 330 could be channeled directly into the data storage module 341 of the data acquisition device 208 and saved for download and analysis at a later time, eliminating the need for wireless transmission of data 206 to the base station 212. Further optionally, all sensor signals 330 could be directed into the data storage module 341 and saved for later download while simultaneously being transmitted to a remote station (not shown) via wireless communication 206 with the base station 212. Although transmission between the data acquisition device 208 and the base station 212 is shown in FIG. 3 as wireless 206, the connection could also be a wired connection in other embodiments of the data acquisition system.

Figure 4:
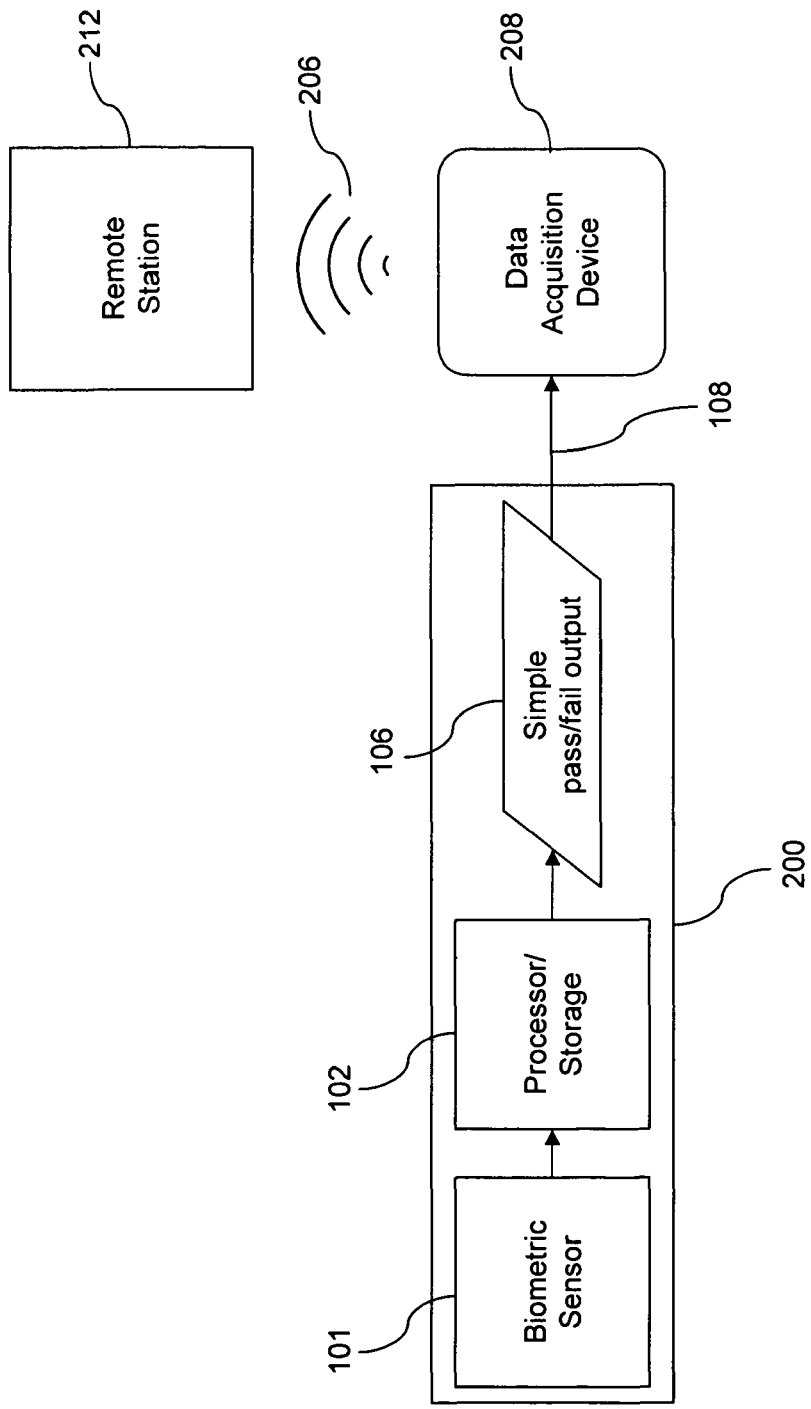
FIG. 4 Block diagram of the biometric sensing device showing the collection and flow of biometric data as it occurs in one embodiment of the present invention.

FIG. 4 is a signal flow diagram showing the flow of biometric data in one embodiment of the present invention. In this embodiment, a biometric sensing device 200 is used to collect and record biometric data and subsequently verify subject identity during the course of a sleep test. In a preferred embodiment, biometric data is collected using a biometric sensor 101 then processed and stored 102 within the biometric sensing device 200. When a subject's identity is verified against the previously collected biometric data during a sleep test, a simple pass/fail result 106 preferably, but not necessarily is output by the biometric sensing device 200 and communicated 108 to the data acquisition device 208 while the biometric identification data itself may remain stored 102 on the biometric sensing device 200. The pass/fail result output 106 by the biometric sensing device 200 may be stored in the data acquisition device 208, wirelessly transmitted to a remote station 206, 212 or a combination of both. In an optional embodiment of the present invention, the biometric sensing device 200 may consist of only a biometric sensor 101 which is capable of capturing biometric data for export to the data acquisition device 208 where it is stored, processed, and subsequently used for subject identification. Although transmission between the data acquisition device 208 and the base station 212 is shown in FIG. 4 as wireless 206, the connection could also be a wired connection in other embodiments of the present invention.

Figure 5:
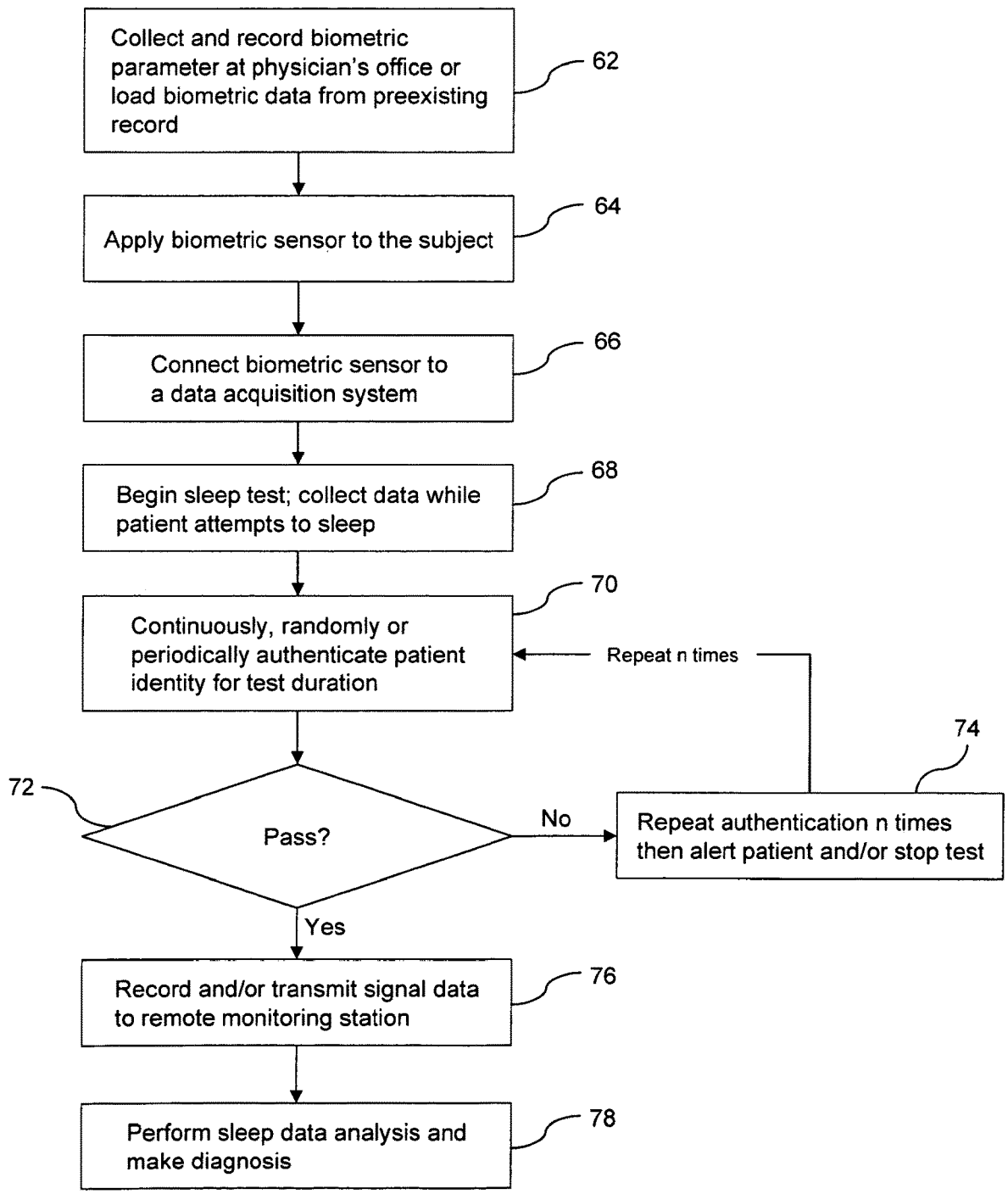
FIG. 5 Flow diagram of one embodiment of the method of biometric verification of identity used in the present invention.

FIG. 5 is a flow chart of one embodiment of the method for using a biometric sensor or sensors to verify a subject's identity during a sleep analysis procedure. Prior to beginning sleep analysis testing, a biometric characteristic or parameter is collected and recorded at the office of the subject's physician or collected from some other reliable, preexisting source 62. Once recorded, this parameter is used by the biometric sensor to verify the subject's identity during the course of the sleep analysis procedure. The biometric sensor is then applied to the subject 64 either by the physician, technician or the like while at the physician's office or by the subject himself at a later time but prior to beginning the sleep analysis test. Either before or after (after shown here) application of the biometric sensor to the subject, the biometric sensor is connected to a data acquisition system 66. Once the biometric sensor and other desired sensors are connected to the data acquisition system, the sleep test can be started when the subject attempts to sleep 68. After starting the sleep test, data collection begins and the biometric sensor verifies subject identity continuously, randomly, or periodically for the duration of the test 70. If at any time during the sleep test the biometric sensor is unable to positively verify the identity of the test subject against the previously recorded biometric data for a pre-specified successive number of attempts, the subject is alerted and/or the sleep analysis test is stopped 72, 74. If subject identity is positively verified, data is recorded and/or transmitted as normal 72, 76. Based on the collected and/or transmitted data a sleep analysis is performed and the subject is diagnosed 78.

FIGS. 6A-D show various preferred embodiments of a biometric sensing device, more specifically a fingerprint sensor, used in the present invention to verify subject identity during the course of sleep analysis and, optionally, to collect biometric data. It is important to note that in each embodiment shown in FIGS. 6A-D, a pulse oximeter is used in combination with a biometric sensing device in such a way that the pulse oximeter is worn on the same hand as the biometric sensing device. As already noted, this serves to ensure that the individual for whom sleep data is being recorded is in fact the individual from whom pulse oximetry data is collected and for whom sleep analysis was intended.

Figure 6A:
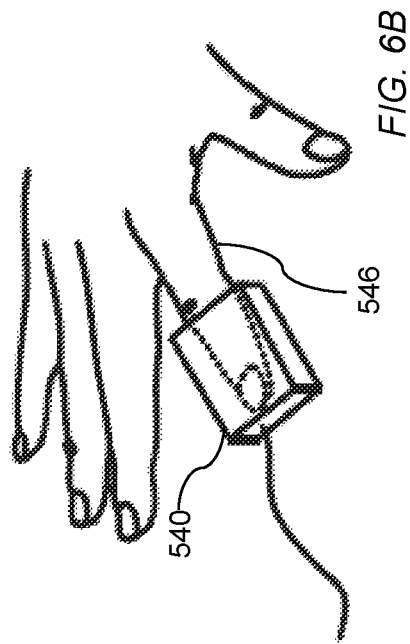
FIGS. 6A-D Perspective views of various embodiments of the applications of the sensors of medical device and method with improved biometric verification of the present invention.
Figure 6B:
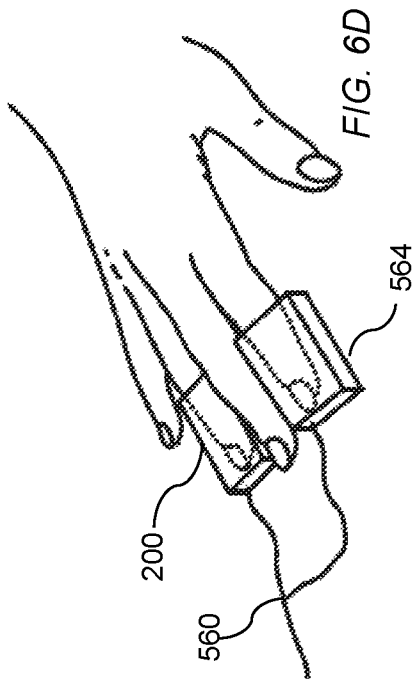

In one embodiment, shown in FIG. 6A and FIG. 6B, a pulse oximeter is used in combination with a biometric sensing device in such a way that biometric verification of subject identity and pulse oximetry are performed on the same digit or finger 540. FIG. 6A provides a cross-sectional view of this embodiment showing a fingerprint sensor 542 positioned to read a subject's fingerprint and a pulse oximeter positioned to collect data from the same digit 544. FIG. 6B provides a perspective view of this embodiment 540 as it could be used on the hand of an individual subject. It should be noted that although this embodiment is shown as being used on a subject's index finger 546, it is not limited to use on this digit and could be used on any other desired digit of the hand. Further, it is envisioned that this embodiment would allow biometric verification and pulse oximetry measurements to occur on the same digit simultaneously or in an alternating fashion.

Figure 6C:
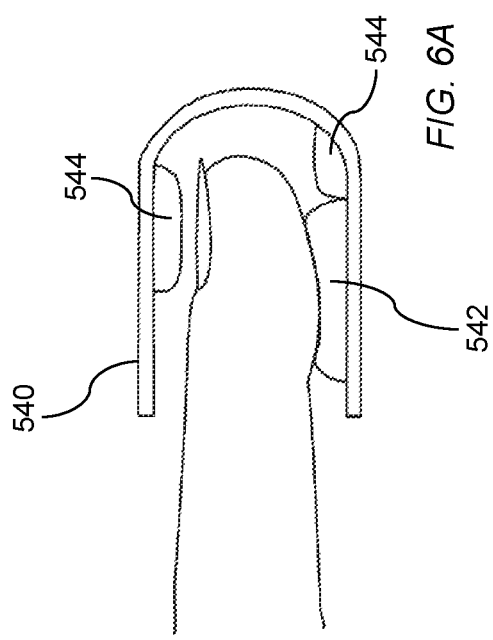

In another embodiment, shown in FIG. 6C, a biometric sensing device and pulse oximeter are used in a shared finger-gripping device 550 in such a way that pulse oximetry and biometric verification must occur on two adjacent digits of the same hand. In this embodiment, it is insignificant on which digit biometric verification of identity occurs and on which digit pulse oximetry occurs. Communication with the data acquisition device in this embodiment is performed through a single connection 552.

Figure 6D:
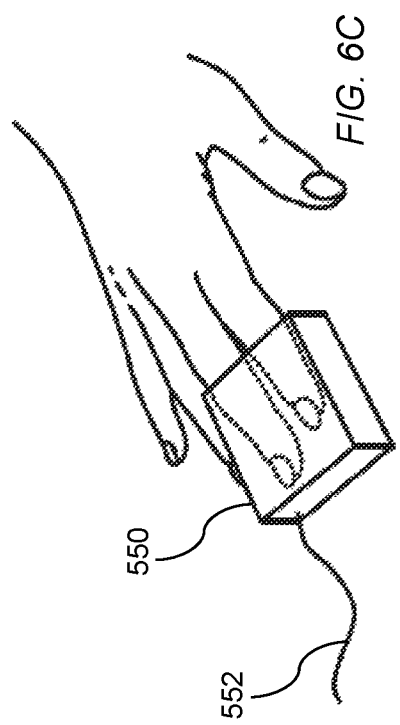

In still another embodiment, shown in FIG. 6D pulse oximetry and biometric verification of identity are performed on separate, optionally non-adjacent digits. In this embodiment, the pulse oximeter 564 is linked to the biometric sensing device 200 by a shared communication connection 560 to the data acquisition device (not shown) in such a way as to require that both devices be used on the same hand. Although in this embodiment the biometric sensing device 200 is linked to the pulse oximeter 564 by a shared communication connection 560 to the data acquisition device (not shown) it is envisioned that various other means could be used to physically link the two devices. For example, the devices need not use a shared communication connection 560 and may communicate with the data acquisition device (not shown) using separate, individual channels. In this case, the two devices could be linked through a different type of physical connection such as a short length of braided polymer or other similar material. Data collected and/or transmitted using any of the various embodiments shown in FIGS. 6A-D, could be transmitted to the data acquisition device (not shown) using a shared, single channel or any combination of multiple channels.

Figure 7:
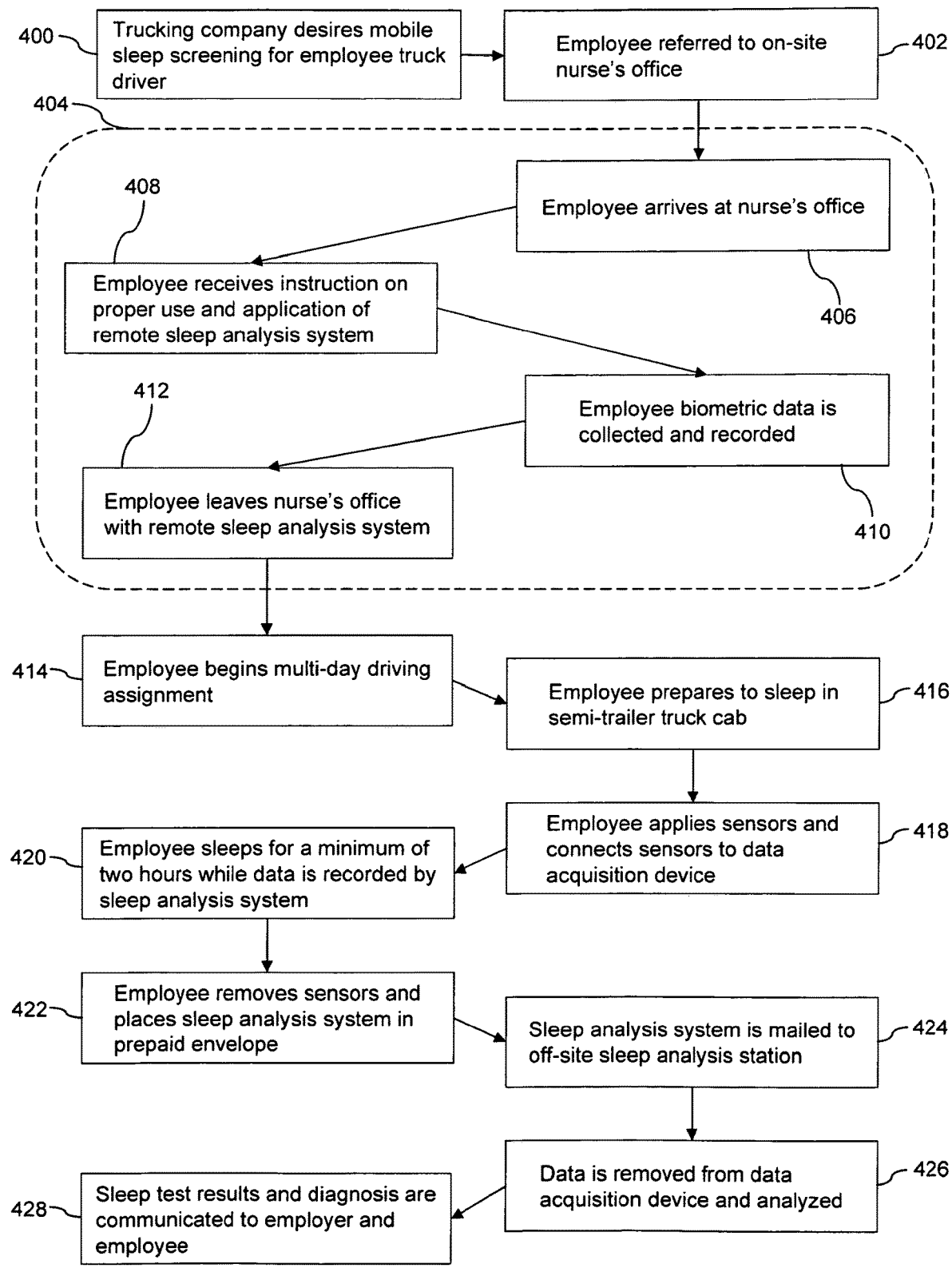
FIG. 7 Flow diagram of an embodiment illustrating a specific occupation-based application of the medical device and method with improved biometric verification.

FIG. 7 is a flow diagram showing one embodiment of the method and process of the present invention. In this embodiment, a trucking company or similar entity desires sleep testing or sleep screening for one or more employees 400. In this embodiment, a single employee truck driver is chosen for sleep screening 400 and subsequently referred to an on-site nurse's office 402. The nurse's office is represented by box 404. After arrival at the nurse's office 406 the employee receives instruction on proper use and application of the sleep analysis system 408. Preferably, this instruction includes printed guides outlining proper use of the system for future reference and review by the employee. Optionally, this instruction could include multimedia references such as instructional digital versatile discs, or the like. After instruction on proper use, employee biometric data is collected and recorded 410 for use in verification of identity during remote sleep testing. Collection of biometric data is preferably performed using the biometric sensing device (shown in FIG. 4). Proper function of the biometric identification step (not shown) is also preferably verified at the time of biometric data collection 410. The employee then leaves the nurse's office carrying the sleep analysis system 412, in this case, comprised of a multi-channel data acquisition device and the proper sensors. In the present embodiment the employee would then return to work and begin a multi-day driving assignment 414. In this case, the employee stops to sleep while still en route to his or her final destination and prepares to sleep in the sleeping area of the cab of the semi-trailer truck 416 which he or she has been operating. Prior to sleep, the employee applies the sensors to his or her actual person and connects the sensors to the data acquisition device 418 according to the provided instructions 408. Sleep data is then recorded by the sleep analysis system for a minimum of two hours of sleep 420. During this time, the employee identity is also verified by the biometric sensing device (shown in FIG. 4). Upon awakening from sleep, the employee removes the sleep sensors and places the sensors and data acquisition device in a prepaid envelope 422 for mailing to an off-site sleep analysis station 424. This envelope is then mailed from a suitable location at the convenience of the employee. Upon receipt of the sleep analysis system at an off-site sleep analysis station, the data is removed from the data acquisition device and analyzed by a technician, clinician, physician, or the like 426 and a diagnosis is made and sent to both employer and employee 428.

Figure 8:
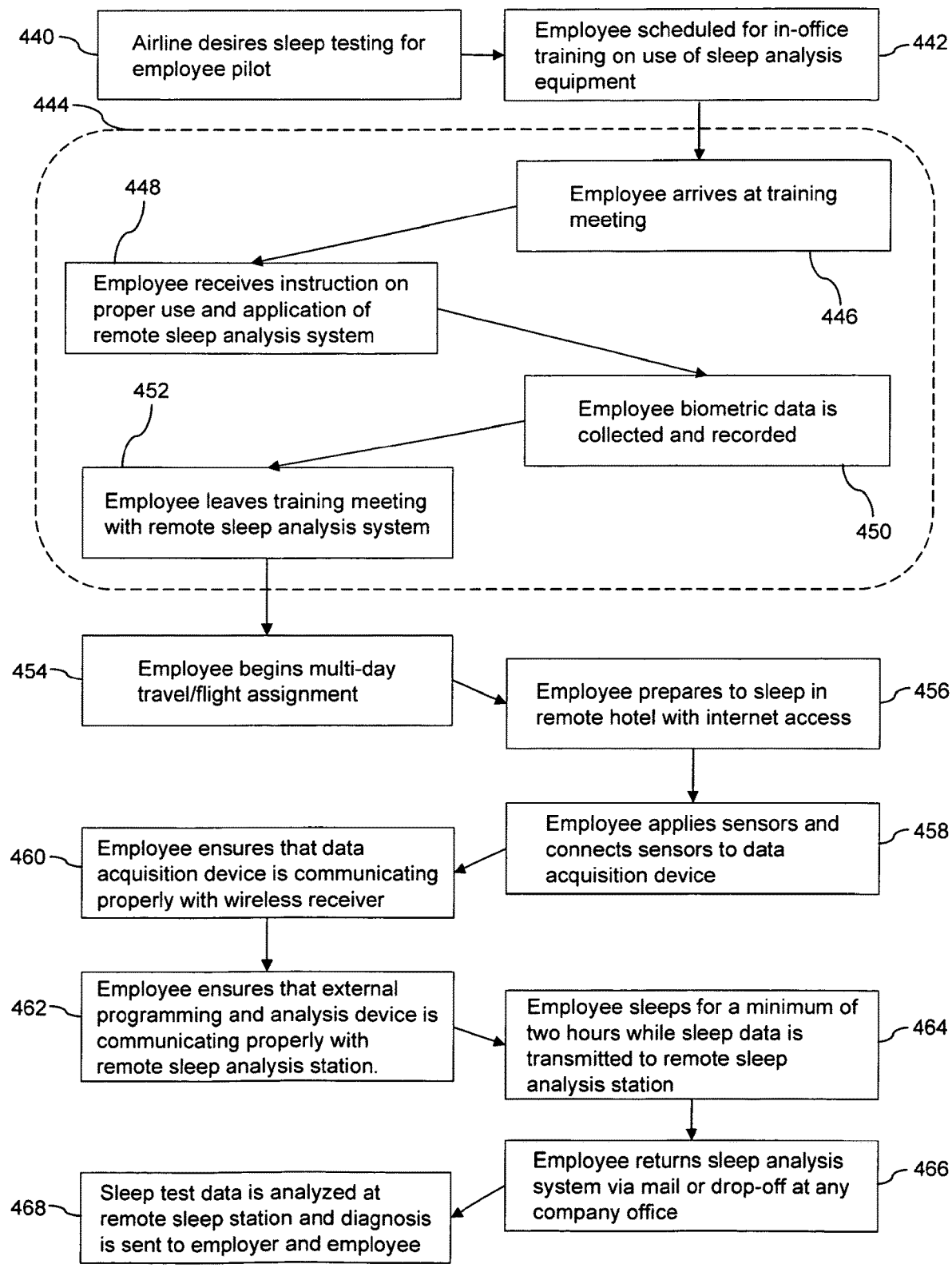
FIG. 8 Flow diagram of another embodiment illustrating a specific occupation-based application of the medical device and method with improved biometric verification.

FIG. 8 is a block diagram showing one envisioned method and process of use for one specific embodiment of the present invention. In this embodiment, an airline or similar entity desires sleep testing or sleep screening for one or more employees 440. Here, a single employee pilot is chosen for sleep screening 440 and subsequently scheduled to attend an in-office training meeting on proper use of sleep analysis equipment 442. The training meeting is represented by box 444. After arrival at the training meeting 446 the employee receives instruction on proper use and application of the sleep analysis system 448. Preferably, this instruction includes printed guides outlining proper use of the system for future reference and review by the employee. Optionally, this instruction could include multimedia references such as instructional digital versatile discs, or the like. After instruction on proper use of the sleep analysis system, employee biometric data is collected and recorded 450 for use in verification of identity during remote sleep testing. Collection of biometric data is preferably performed using the biometric sensing device (shown in FIG. 4). Proper function of the biometric identification step (not shown) is also preferably verified at the time of biometric data collection 450. The employee then leaves the training meeting carrying the sleep analysis system 452, in this case, comprised of a multi-channel data acquisition device capable of wireless communication, a wireless communication receiver, an external programming and analysis device (e.g. a notebook computer) and the proper sleep sensors. In the present embodiment, the employee would then return to work and begin a multi-day travel/flight assignment 454. In this case, the employee stops to sleep during the travel/flight assignment at a hotel with internet access 456 or access to another similar communication system. Prior to sleep, the employee applies the sensors to his or her actual person and connects the sensors to the data acquisition device 458 according to the provided instructions 448. Further, the employee ensures that the wireless communication between the data acquisition device and the wireless receiver station is function properly 460 and that data transmission and communication between the external programming device and remote sleep analysis station is functioning properly 462. In a preferable embodiment, telephone or other live communication support is available for the steps of connecting the sleep analysis system 458, 460, 462. Sleep data is then recorded and transmitted to a remote sleep analysis station by the sleep analysis system for a minimum of two hours of sleep 464. During this time, employee identity is also verified by the biometric sensing device (shown in FIG. 4). Upon awakening from sleep, the employee removes the sleep sensors and returns the sleep analysis system using a prepaid mailing package or by drop-off at any company office. The data transmitted in 464 is analyzed either in real-time, during transmission, or at some time shortly afterward by a technician, clinician, physician, or the like and a diagnosis is made and sent to both employer and employee 468.

Figure 9:
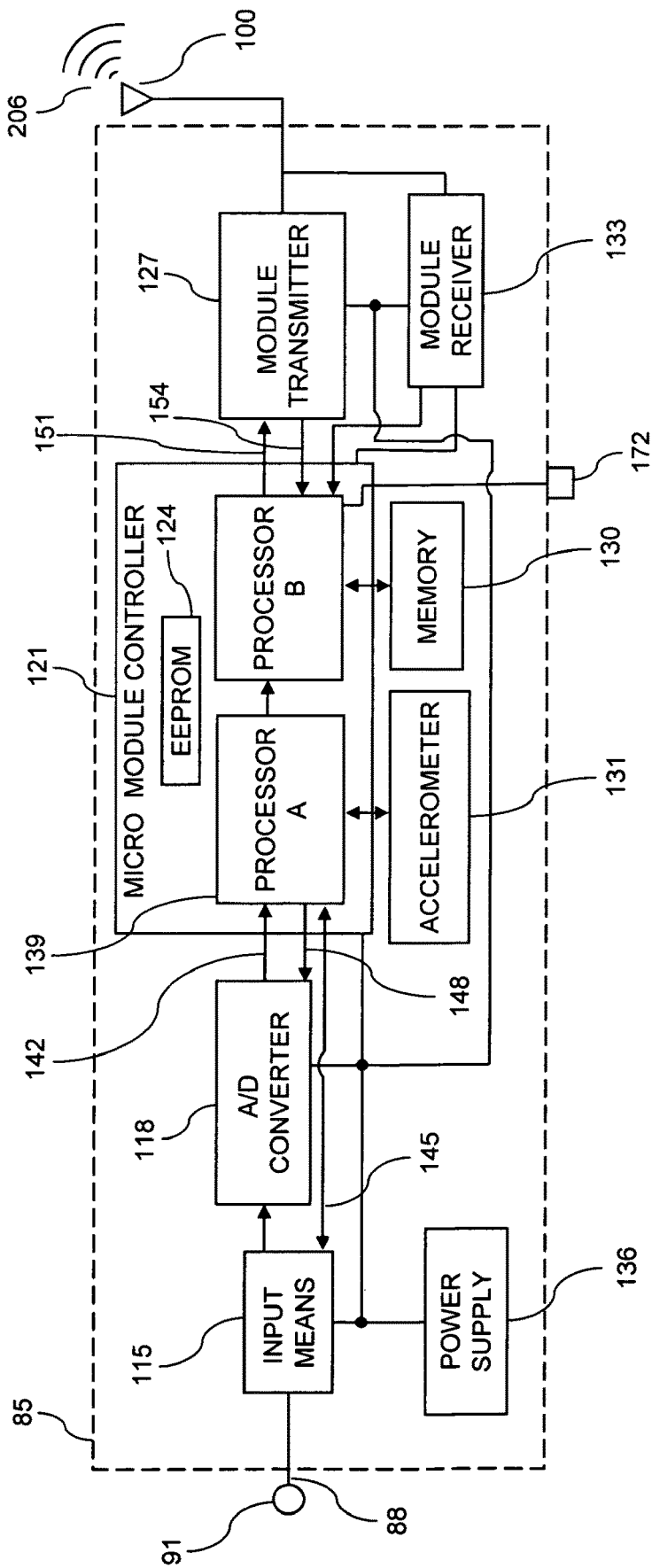
FIG. 9 Block diagram illustrating the data acquisition and data handling device and processes used in one embodiment of the present invention.

Referring now to FIG. 9, there is shown a more detailed block diagram of the signal processing module 85 of the data acquisition device (shown in FIG. 3) with the sensor or sensors 91 and the module antenna 100. The signal processing module 85 comprises input means 115, analog-to-digital (A/D) means 118, a module microcontroller 121 with a nonvolatile memory, advantageously, an EEPROM 124, a module transmitter 127, a connection to removable memory 130, a module receiver 133 and a module power supply 136. Although the module antenna 100 is shown externally located from the signal processing module 85, it can also be incorporated therein. A module power supply 136 provides electrical power to the signal processing module 85. Additionally the signal processing module 85 will preferably contain an accelerometer 131 connected to a microprocessor 139 for position detection, motion detection, and motion artifact correction.

The input means 115 is adjustable either under control of the module microcontroller 121 or by means of individually populatable components based upon the specific external input 88 (i.e. a signal from any sensor) characteristics and range enabling the input means 115 to accept that specific external input 88.

After receipt by the input means 115, the external input 88 is inputted to the A/D means 118. The A/D means 118 converts the input to a digital signal 142 and conditions it. The A/D means 118 utilizes at least one programmable A/D converter. This programmable A/D converter may be an AD7714 as manufactured by Analog Devices or similar. Depending upon the application, the input means 115 may also include at least one low noise differential preamp. This preamp may be an INA126 as manufactured by Burr-Brown or similar. The module microcontroller 121 can be programmed to control the input means 115 and the A/D means 118 to provide specific number of external inputs 88, sampling rate, filtering and gain. These parameters are initially configured by programming the module microcontroller 121 to control the input means 115 and the A/D means 118 via input communications line 145 and A/D communications line 148 based upon the input characteristics and the particular application. If different sensors are used, the A/D converter is reconfigured by reprogramming the module microcontroller 121.

The module microcontroller 121 controls the operation of the signal processing module 85. In the present embodiment, the module microcontroller 121 includes a serial EEPROM 124 but any nonvolatile memory (or volatile memory if the signal processing module remains powered) can be used. The EEPROM 124 can also be a separate component external to the module microcontroller 121. The module microcontroller may advantageously contain two microprocessors in series as shown in FIG. 9. The module microcontroller 121 is programmed by the external programming means (shown in FIG. 1) through the connector 172 or through radio frequency signal from the base station (shown in FIG. 3). The same module microcontroller 121, therefore, can be utilized for all applications and inputs by programming it for those applications and inputs. If the application or inputs change, the module microcontroller 121 is modified by merely reprogramming. The digital signal 142 is inputted to the module microcontroller 121. The module microcontroller 121 formats the digital signal 142 into a digital data stream 151 encoded with the data from the digital signal 142. The digital data stream 151 is composed of data bytes corresponding to the encoded data and additional data bytes to provide error correction and housekeeping functions. The digital data stream 151 is used to modulate the carrier frequency generated by the transmitter 127.

The module transmitter 127 is under module microcontroller 121 control. The module transmitter 127 employs frequency synthesis to generate the carrier frequency. In the preferred embodiment, this frequency synthesis is accomplished by a voltage controlled crystal reference oscillator and a voltage controlled oscillator in a phase lock loop circuit. The digital data stream 151 is used to frequency modulate the carrier frequency resulting in the wireless data transmission signal 206 which is then transmitted through the module antenna 100. The generation of the carrier frequency is controlled by the module microcontroller 121 through programming in the EEPROM 124, making the module transmitter 127 frequency agile over a broad frequency spectrum. In the United States and Canada a preferred operating band for the carrier frequency is 902 to 928 MHz. The EEPROM 124 can be programmed such that the module microcontroller 121 can instruct the module transmitter 127 to generate a carrier frequency in increments between 902 to 928 MHz. as small as about 5 to 10 kHz. In the US and other countries of the world, the carrier frequency may be in the 902-928 MHz, Wireless Medical Telemetry Bands (WMTS), 608-614 MHz, 1395-1400 MHz, or 1429-1432 MHz or other authorized band. This allows the system to be usable in non-North American applications and provides additional flexibility.

The voltage controlled crystal oscillator (not shown) in the module transmitter 127, not only provides the reference frequency for the module transmitter 127 but, advantageously also provides the clock function 154 for the module microcontroller 121 and the A/D means 118 assuring that all components of the signal processing module 85 are synchronized. An alternate design can use a plurality of reference frequency sources where this arrangement can provide certain advantages such as size or power consumption in the implementation. The module receiver 133 in the signal processing module 85 receives RF signals from the base station (shown in FIG. 3). The signals from the base station can be used to operate and control the signal processing module 85 by programming and reprogramming the module microprocessor 121 and EEPROM 124 therein.

Optionally, the signal processing module 85 of the data acquisition device (shown in FIG. 3) may include an output means (not shown). For example, the processor 139 may have a connection to an output means through which processed digital information could be passed to an external device, such as a fingerprint sensing device, in order to modulate the function of the external device. In another embodiment, digital information may pass first through the A/D converter 118 and be converted to analog format prior to being sent via the output means to an external analog device.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

I claim:

1. A remote or home sleep diagnostic system comprising a device and a database, the database remote from a test location, for an unattended sleep test, the system adapted for providing sleep test data from the database for analysis and diagnosing sleep apnea, the device further comprising a portable, wearable patient interface box with at least three sensors for measuring physiological parameters of a subject related to the subject's quality of sleep, the at least three sensors being an air flow or snore sensor, a pulse oximeter sensor and a respiratory effort sensor, a processor and at least one biometric sensor for identifying the subject, wherein the portable, wearable interface box houses the processor having circuitry adapted to connect the at least three sensors and the biometric sensor to the processor to collect data for identification of the subject being tested using the data from the biometric sensor, the at least one biometric sensor is adapted to randomly collect data to authenticate the identity of the subject being tested during a sleep test, and the collected data is uploaded from the portable, wearable patient interface box to the database for further output in a form for analysis and diagnosis by a clinician.

2. The system of claim 1, wherein the processor or another processor is adapted to use previously collected biometric data of the subject to verify the subject's identity who took the sleep test.

3. The system of claim 1 wherein the system is adapted to compare the collected biometric data with previously collected biometric data, and is adapted to securely exchange information to comply with HIPAA requirements with an external device through a transceiver on the system.

4. The system of claim 1, wherein the at least one biometric sensor is adapted to collect biometric data from a subject, the processor or another processor is adapted to compare the collected biometric data previously collected from the subject, and the processor or the another processor is adapted to output verification of the identity of the subject whose quality of sleep is being measured without outputting the subject's biometric data.

5. The system of claim 1 wherein the at least one biometric sensor is selected from the group of sensors consisting of fingerprint sensors, facial recognition sensors, hand geometry sensors, iris and retinal sensors, and voice recognition sensors.

6. The system of claim 1 further including a transceiver or transmitter adapted to transmit the data from the at least one biometric sensor and/or the at least three sensors to the database at remote location.

7. The system of claim 1, wherein the biometric sensor is a fingerprint sensor.

8. A remote or home sleep diagnostic system comprising a device and a database, the database remote from a test location, for an unattended sleep test, the system adapted for providing sleep test data from the database for analysis and diagnosing sleep apnea, the device further comprising an portable, wearable patient interface box with at least three sensors for measuring physiological parameters of a subject related to the subject's quality of sleep, the at least three sensors being an air flow or snore sensor, a blood oxygenation sensor and a respiratory effort sensor, a processor and at least one biometric sensor for identifying the subject wherein the portable, wearable patient interface box houses the processor having circuitry adapted to connect the at least three sensors and the biometric sensor to the processor, to collect data for identification of the subject being tested using the data from the biometric sensor to compare with biometric data previously collected from the subject, and to upload the collected data from the portable, wearable patient interface box to the database for further output in a form for analysis and diagnosis by a clinician.

9. The system of claim 8, wherein authentication of subject identity by said biometric sensor is performed randomly.

10. The system of claim 8, wherein the system is adapted to use previously collected biometric data of the subject to verify the subject identity with the processor during the course of the sleep test.

11. The system of claim 8, wherein the system is adapted to compare the collected biometric data with previously collected biometric data, and is adapted to securely exchange information to comply with HIPAA requirements with an external device through a transceiver on the system.

12. The system of claim 8, wherein the biometric sensor is adapted to detect a biometric electrophysiological characteristic of the subject.

13. The system of claim 8, the system further comprising a memory for storing biometric data of the subject for comparison.

14. The system of claim 8 wherein the at least one biometric sensor is selected from the group of sensors consisting of fingerprint sensors, facial recognition sensors, hand geometry sensors, iris and retinal sensors, and voice recognition sensors.

15. A remote or home sleep diagnostic system comprising a device and a database, the database remote from a test location, for an unattended sleep test, the system adapted for providing sleep test data for analysis and diagnosing sleep apnea, the device further comprising a portable, wearable patient interface box with at least three sensors for measuring physiological parameters of a subject related to the subject's quality of sleep, the at least three sensors being an air flow or snore sensor, a blood oxygenation sensor and a respiratory effort sensor, a processor and at least one biometric sensor for identifying the subject wherein the biometric sensor is adapted to detect a biometric electrophysiological characteristic of the subject and the portable, wearable patient interface box houses the processor having circuitry adapted to connect the at least three sensors and the biometric sensor to the processor, to collect data for identification of the subject being tested using the data from the biometric sensor to compare with biometric data previously collected from the subject, and to upload the collected data from the portable, wearable patient interface box to the database for further output in a form for analysis and diagnosis by a clinician.

16. The system of claim 15, wherein authentication of subject identity by said biometric sensor is performed randomly.

17. The system of claim 15 wherein the at least one biometric sensor is selected from the group of sensors consisting of fingerprint sensors, facial recognition sensors, hand geometry sensors, iris and retinal sensors, and voice recognition sensors.

18. The system of claim 15, compares the collected biometric data with the biometric data previously collected from the subject, and the processor outputs verification of the identity of the subject whose quality of sleep is being measured without outputting the subject's biometric data.

19. The system of claim 18, wherein biometric data is loaded onto the sleep diagnostic device from an already existent source.

20. The system of claim 15, wherein the biometric sensor is a EKG sensor.

* * * * *